(12) United States Patent
Goueli et al.

(10) Patent No.: US 7,195,884 B2
(45) Date of Patent: Mar. 27, 2007

(54) METHODS AND KITS FOR TRANSFERASES

(75) Inventors: Said A. Goueli, Fitchburg, WI (US); Robert F. Bulleit, Verona, WI (US)

(73) Assignee: Promega Corp., Madison, WI (US)

( * ) Notice: Subject to any disclaimer, the term of this patent is extended or adjusted under 35 U.S.C. 154(b) by 57 days.

(21) Appl. No.: 10/199,970

(22) Filed: Jul. 19, 2002

(65) Prior Publication Data

US 2004/0014159 A1   Jan. 22, 2004

(51) Int. Cl.
*C12Q 1/48* (2006.01)
*C12Q 1/42* (2006.01)
*C12N 9/12* (2006.01)
*C12N 9/16* (2006.01)

(52) U.S. Cl. .......................... 435/15; 435/21; 435/24; 435/193; 435/194; 435/196

(58) Field of Classification Search .............. 435/15, 435/21, 24, 193, 194, 196
See application file for complete search history.

(56) References Cited

U.S. PATENT DOCUMENTS

| | | | |
|---|---|---|---|
| 4,557,862 A * | 12/1985 | Mangel et al. ............... | 530/331 |
| 5,120,644 A | 6/1992 | Ikenaka et al. | |
| 5,439,797 A | 8/1995 | Tsien et al. | |
| 5,759,787 A | 6/1998 | Strulovici | |
| 5,763,198 A | 6/1998 | Hirth et al. | |
| 5,854,011 A * | 12/1998 | Chen et al. ................... | 435/24 |
| 5,869,275 A | 2/1999 | Huang | |
| 5,917,012 A | 6/1999 | Nishikata .................... | 530/227 |
| 6,066,462 A | 5/2000 | Goueli | |
| 6,153,591 A | 11/2000 | Cai et al. | |
| 6,184,210 B1 | 2/2001 | Keana et al. | |
| 6,203,994 B1 | 3/2001 | Epps et al. | |
| 6,248,550 B1 | 6/2001 | Tsien et al. | |
| 6,248,904 B1 | 6/2001 | Zhang et al. | |
| 6,280,965 B1 | 8/2001 | Rathinavelu et al. | |
| 6,335,429 B1 | 1/2002 | Cai et al. | |
| 6,342,611 B1 | 1/2002 | Weber et al. | |
| 6,348,310 B1 | 2/2002 | Goueli | |
| 6,355,618 B1 | 3/2002 | Cai et al. | |
| 6,410,255 B1 | 6/2002 | Pollock et al. | |
| 2002/0004214 A1 | 1/2002 | Goldschmidt et al. | |

FOREIGN PATENT DOCUMENTS

| | | |
|---|---|---|
| EP | 1 182 263 | 2/2002 |
| JP | 09-285297 | 11/1997 |
| JP | 2001-019700 | 1/2001 |
| WO | WO 98/11251 | 3/1998 |
| WO | WO 00/31291 | 6/2000 |
| WO | WO 00/66766 | 11/2000 |
| WO | WO 01/25477 | 4/2001 |

OTHER PUBLICATIONS

S. Kawabata et al. "Highly Sensitive Peptide-4-Methylcoumaryl-7-Amide Substrates For Blood Clotting Proteases and Trypsin", Eur. J. Biochem. 172: 17-25 (1988).*

J.K. McDonald et al. "New Observations on the Substrate Specificity of Cathepsin C (Dipeptidyl Aminopeptidase I)", J. Biol. Chem. 244(10): 2693-2709. (May 1969).*

Fernandez Murray, P., Hammerschmidt, P., Samela, A., Passeron, S., *Peptide Degradation: Effect of Substrate Phosphorylation on Aminopeptidasic Hydrolysis*, Int. J. Biochem. Cell Biol., vol. 28, No. 4, pp. 451-456 (1996).

Leytus, S.P., Patterson, W.L., and Mangel, W.F., *New class of sensitive and selective fluorogenic substrates for serine proteinases*, Biochem. J. 215, pp. 253-260 (1983).

Leytus, S.P., Melhado, L.L., and Mangel, W.F., *Rhodamine-based compounds as fluorogenic substrates for serine proteinases*, Biochem. J. 209, pp. 299-307 (1983).

Liu, J., Bhalgat, M., Zhang, C., Diwu, Z., Hoyland, B., and Klaubert, D., *Fluorescent molecular probes V: A sensitive caspase-3 substrate for fluorometric assays*, Bioorganic & Medicinal Chemistry Letters 9, pp. 3231-3236 (1999).

Dass C. and Mahalakshmi P., *Phosphorylation of enkephalins enhances their proteolytic stability*, Life Sciences, vol. 58, No. 13, pp. 1039-1045 (1996).

Taylor, A., *Aminopeptidaes: structure and function*, The FASEB Journal, vol. 7, pp. 290-298 (Feb. 1993).

Sjöström, H., Norén and Olsen, J., *Structure and function of aminopeptidase N*, in Cellular Peptidases in Immune Functions and Diseases 2, pp. 25-34 (Langer & Ansorge, eds., 2000).

Doucette, A. and Li, L., *Investigation of the applicability of a sequential digestion protocol using trypsin and leucine aminopeptidase M for protein identification by matix-assisted laser desorption/ionization—time of flight mass spectrometry*, Proteomics, 1, pp. 987-1000 (2001).

Helene, A., Beaumont, A, and Roques, B.P., *Functional residues at the active site of aminopeptidase N*, Eur. J. Biochem. 196, pp. 385-393 (1991).

Van Wart, H.E. and Lin, S.H., *Metal binding stoichiometry and mechanism of metal ion modulation of the activity of porcine kidney leucine aminopeptidase*, Biochemistry, 20, pp. 5682-5689 (1981).

McDonald, J.K., Zeitman, B.B., Reilly, T.J., and Ellis, S., *New observations on the substrate specificity of cathepsin C (dipeptidyl aminopeptidase I)*, The Journal of Biological Chemistry, vol. 244, No. 10, pp. 2693-2709 (May 25, 1969).

(Continued)

*Primary Examiner*—Rebecca E. Prouty
(74) *Attorney, Agent, or Firm*—Whyte Hirschboeck Dudek S.C.

(57) ABSTRACT

A method for detecting transferase activity of a sample includes contacting the sample with a substrate and at least one of a phosphate group donor and a phosphate group acceptor. The substrate includes a reporter compound and amino acids. A peptidase is added that cleaves a non-phosphorylated substrate at a first rate and a phosphorylated substrate and a second rate. The output of the reporter compound is detected. In a preferred embodiment, the transferase activity detected is a kinase activity. In another preferred embodiment, the transferase activity detected is a phosphatase activity. Also provided is a method of screening for alterations in a transferase reaction. Kits and peptide substrate are also provided for carrying out at least one of the methods of the invention.

16 Claims, 10 Drawing Sheets

OTHER PUBLICATIONS

Metrione, R.M., Neves, A.G., and Fruton, J.S., *Purification and properties of dipeptidyl Transferase*, Biochemistry, vol. 5, pp. 1597-1604 (May 1966).

Byun, T., Kofod, L., and Blinkovsky, A., *Synergistic action of an X-prolyl dipeptidyl aminopeptidase and a non-specific aminopeptidase in protein hydrolysis*, J. Agric. Food Chem., 49, pp. 2061-2063 (2001).

Horn, M., Pavlik, M., Doleckova, L., Baudys, M. and Mares, M., *Arginine-based structures are specific inhibitors of cathepsin C—application of peptide combinatorial libraries*, Eur. J. Biochem. 267, pp. 3330-3336 (2000).

Blinkovsky, A.M., Byun, T., Brown, K.M., Golightly, E.J., and Klotz., A.V., *A non-specific aminopeptidase from Aspergillus*, Biochimica et Biophysica Acta 1480, pp. 171-181 (2000).

Turner, A.J., *Membrane alanyl aminopeptidase*, in Handbook of Proteolytic Enzymes, pp. 996-1000 (Barrett, A.J., Rawlings, N.D., & Woessner, J.F., eds., 1998).

Thorsett, E.G. and Wyvratt, M.J., *Inhibition of Zinc peptidases that hydrolyse neuropeptides*, in Neuropeptides and Their Peptidases, 229-292 (Turner, A.J., ed., 1987).

*Cytosol aminopeptidase signature*, http://srs.ebi.ac.uk/srs6bin/cgi-bin/wgetz?-e-[prositedoc-ID:PDOC00548] (Jan. 2002).

Calzyme Laboratories Inc., *Leucine Aminopeptidase*, http://www.calzyme.com/catalog/leucamin.html (Jan. 2002).

Calbiochem, *Protease Inhibitors*, http://www.calbiochem.com/Products/ProductDetail_CBCB.asp?catNO=230790 (Aug. 2001).

Jayawardene, D.S., et al., *The effect of N-terminal acetylation and the inhibition activity of acetylated enkephalins on the aminopeptidase M-catalyzed hydrolysis of enkephalins*, Peptides 20, pp. 963-970 (1999).

Cai, S.X., et al., *Design and Synthesis of Rhodamine 110 Derivative and Caspase-3 Substrate for Enzyme and Cell-Based Fluorescent Assay*, Bioorganic & Medicinal Chemistry Letters 11, pp. 39-42 (2001).

Tozsser, J., et al., *Effect of Serine and Tyrosine Phosphorylation on Retroviral Proteinase Substrates*, Eur. J. Biochem, 265, pp. 423-429 (1999).

R. Premont, et al. "Identification, Purification, and Characterization of GRK5, a Member of the Family of G Protein-coupled Receptor Kinases", J. Biol. Chem. 269(9); Mar. 4, 1994, pp. 6832-6841.

J. Peters, et al. "Syk, Activated by Cross-linking the B-cell Antigen Receptor, Localizes to the Cytosol Where It Interacts with and Phosphorylates a-Tubulin on Tyrosin", J. Biol. Chem. 271(9); Mar. 1, 1996, pp. 4755-4762.

H. Umetsu, et al. "Purification, crystallisation and characterisation of carboxypeptidase from wheat bran", Food Chem. vol. 7, Issue 2, Sep. 1981, pp. 125-138.

Elastin Products Company website; http://www.elastin.com; Carboxypeptidase W, No. CBW196 (Mar. 2006).

* cited by examiner

SEQUENCE LISTING

<160> NUMBER OF SEQ ID NOS: 34

<210> SEQ ID NO 1
<211> LENGTH: 7
<212> TYPE: PRT

```
<213> ORGANISM: Artificial Sequence
<220> FEATURE:
<223> OTHER INFORMATION: synthetic peptide

<400> SEQUENCE: 1

Leu Arg Arg Ala Ser Leu Gly
1               5

<210> SEQ ID NO 2
<211> LENGTH: 11
<212> TYPE: PRT
<213> ORGANISM: Artificial Sequence
<220> FEATURE:
<223> OTHER INFORMATION: synthetic peptide

<400> SEQUENCE: 2

Lys Lys Ala Leu Arg Arg Ala Ser Leu Lys Gly
1               5                   10

<210> SEQ ID NO 3
<211> LENGTH: 11
<212> TYPE: PRT
<213> ORGANISM: Artificial Sequence
<220> FEATURE:
<223> OTHER INFORMATION: synthetic peptide

<400> SEQUENCE: 3

Lys Lys Ala Leu Arg Lys Ala Ser Val Arg Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic peptide

<400> SEQUENCE: 4

Tyr Ile Tyr Gly Ala Phe Lys Arg Arg Gly
1               5                   10

<210> SEQ ID NO 5
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: phosphorylated
<222> LOCATION: (4)..(4)
<223> OTHER INFORMATION:

<400> SEQUENCE: 5

Arg Arg Ala Thr Val Ala
1               5

<210> SEQ ID NO 6
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: phosphorylated
<222> LOCATION: (3)..(3)
<223> OTHER INFORMATION:

<400> SEQUENCE: 6
```

```
Tyr Ile Tyr Gly Ala Phe Lys Arg Arg Gly
1               5                   10

<210> SEQ ID NO 7
<211> LENGTH: 5
<212> TYPE: PRT
<213> ORGANISM: Artificial Sequence
<220> FEATURE:
<223> OTHER INFORMATION: synthetic peptide; X at positions 1, 3, and 4
      is any amino acid; X at position 5 is Ser or Thr.
<220> FEATURE:
<221> NAME/KEY: MISC_FEATURE
<222> LOCATION: (1)..(1)
<223> OTHER INFORMATION: X is any amino acid at position 1.
<220> FEATURE:
<221> NAME/KEY: MISC_FEATURE
<222> LOCATION: (3)..(4)
<223> OTHER INFORMATION: X is any amino acid at positions 3 and 4.
<220> FEATURE:
<221> NAME/KEY: MISC_FEATURE
<222> LOCATION: (5)..(5)
<223> OTHER INFORMATION: X is either Ser or Thr at position 5.

<400> SEQUENCE: 7

Xaa Arg Xaa Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide;
<220> FEATURE:
<221> NAME/KEY: MISC_FEATURE
<222> LOCATION: (1)..(1)
<223> OTHER INFORMATION: X is any amino acid at position 1
<220> FEATURE:
<221> NAME/KEY: MISC_FEATURE
<222> LOCATION: (3)..(4)
<223> OTHER INFORMATION: X is any amino acid at positions 3 and 4
<220> FEATURE:
<221> NAME/KEY: MISC_FEATURE
<222> LOCATION: (5)..(5)
<223> OTHER INFORMATION: X is Ser or Thr at position 5

<400> SEQUENCE: 8

Xaa Arg Xaa Xaa Xaa Val
1               5

<210> SEQ ID NO 9
<211> LENGTH: 4
<212> TYPE: PRT
<213> ORGANISM: Artificial Sequence
<220> FEATURE:
<223> OTHER INFORMATION: sythetic peptide
<220> FEATURE:
<221> NAME/KEY: MISC_FEATURE
<222> LOCATION: (1)..(1)
<223> OTHER INFORMATION: phosphorylated amino acid at position 1
<220> FEATURE:
<221> NAME/KEY: MISC_FEATURE
<222> LOCATION: (2)..(3)
<223> OTHER INFORMATION: X is any amino acid at postions 2 and 3
<220> FEATURE:
<221> NAME/KEY: MISC_FEATURE
<222> LOCATION: (4)..(4)
<223> OTHER INFORMATION: X is Ser or Thr at postion 4

<400> SEQUENCE: 9

Ser Xaa Xaa Xaa
1
```

```
<210> SEQ ID NO 10
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is Ser or Thr at position 1
<220> FEATURE:
<221> NAME/KEY: MISC_FEATURE
<222> LOCATION: (2)..(3)
<223> OTHER INFORMATION: X is any amino acid at positions 2 and 3
<220> FEATURE:
<221> NAME/KEY: MISC_FEATURE
<222> LOCATION: (5)..(5)
<223> OTHER INFORMATION: X is any amino acid at position 5

<400> SEQUENCE: 10

Xaa Xaa Xaa Glu Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Ser or Thr
<220> FEATURE:
<221> NAME/KEY: MISC_FEATURE
<222> LOCATION: (2)..(3)
<223> OTHER INFORMATION: X at positions 2 and 3 is any amino acid
<220> FEATURE:
<221> NAME/KEY: MISC_FEATURE
<222> LOCATION: (5)..(5)
<223> OTHER INFORMATION: X at position 5 is any amino acid

<400> SEQUENCE: 11

Xaa Xaa Xaa Asp Xaa
1               5

<210> SEQ ID NO 12
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: X at position 2 is any amino acid

<400> SEQUENCE: 12

Arg Xaa Ser
1

<210> SEQ ID NO 13
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: X at position 3 is any amino acid
```

```
<400> SEQUENCE: 13

Arg Arg Xaa Ser
1

<210> SEQ ID NO 14
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(3)
<223> OTHER INFORMATION: X at position 2 and 3 is any amino acid

<400> SEQUENCE: 14

Arg Xaa Xaa Ser
1

<210> SEQ ID NO 15
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(4)
<223> OTHER INFORMATION: X at positions 3 and 4 is any amino acid

<400> SEQUENCE: 15

Lys Arg Xaa Xaa Ser
1               5

<210> SEQ ID NO 16
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Arg or Lys
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is Ser or Thr

<400> SEQUENCE: 16

Xaa Xaa Xaa
1

<210> SEQ ID NO 17
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Arg or Lys
<220> FEATURE:
<221> NAME/KEY: MISC_FEATURE
<222> LOCATION: (2)..(3)
<223> OTHER INFORMATION: X at positions 2 and 3 is any amino acid
```

-continued

```
<220> FEATURE:
<221> NAME/KEY: MISC_FEATURE
<222> LOCATION: (4)..(4)
<223> OTHER INFORMATION: X at position 4 is Ser or Thr

<400> SEQUENCE: 17

Xaa Xaa Xaa Xaa
1

<210> SEQ ID NO 18
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: X at positions 1 and 2 is Arg or Lys
<220> FEATURE:
<221> NAME/KEY: MISC_FEATURE
<222> LOCATION: (3)..(3)
<223> OTHER INFORMATION: X at position3 is any amino acid
<220> FEATURE:
<221> NAME/KEY: MISC_FEATURE
<222> LOCATION: (4)..(4)
<223> OTHER INFORMATION: X at position 4 is Ser or Thr

<400> SEQUENCE: 18

Xaa Xaa Xaa Xaa
1

<210> SEQ ID NO 19
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Arg or Lys
<220> FEATURE:
<221> NAME/KEY: MISC_FEATURE
<222> LOCATION: (2)..(4)
<223> OTHER INFORMATION: X at positions 2, 3, 4 is any amino acid
<220> FEATURE:
<221> NAME/KEY: MISC_FEATURE
<222> LOCATION: (5)..(5)
<223> OTHER INFORMATION: X at position 5 is Ser or Thr

<400> SEQUENCE: 19

Xaa Xaa Xaa Xaa Xaa
1               5

<210> SEQ ID NO 20
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Ser or Thr
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is Arg or Lys
```

```
<400> SEQUENCE: 20

Xaa Xaa Xaa
1

<210> SEQ ID NO 21
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(4)
<223> OTHER INFORMATION: X at position 2, 3, 4 is any amino acid
<220> FEATURE:
<221> NAME/KEY: MISC_FEATURE
<222> LOCATION: (5)..(5)
<223> OTHER INFORMATION: Ser at position is phosphorylated

<400> SEQUENCE: 21

Ser Xaa Xaa Xaa Ser
1               5

<210> SEQ ID NO 22
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Ser or Thr
<220> FEATURE:
<221> NAME/KEY: MISC_FEATURE
<222> LOCATION: (3)..(3)
<223> OTHER INFORMATION: X at position 3 is any amino acid
<220> FEATURE:
<221> NAME/KEY: MISC_FEATURE
<222> LOCATION: (4)..(4)
<223> OTHER INFORMATION: X at position 4 is Lys or Arg

<400> SEQUENCE: 22

Xaa Pro Xaa Xaa
1

<210> SEQ ID NO 23
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Lys or Arg
<220> FEATURE:
<221> NAME/KEY: MISC_FEATURE
<222> LOCATION: (2)..(2)
<223> OTHER INFORMATION: X at position 2 is Ser or Thr

<400> SEQUENCE: 23

Xaa Xaa Pro
1

<210> SEQ ID NO 24
<211> LENGTH: 3
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Ser or Thr
<220> FEATURE:
<221> NAME/KEY: MISC_FEATURE
<222> LOCATION: (3)..(3)
<223> OTHER INFORMATION: X at position 3 is Lys or Arg

<400> SEQUENCE: 24

Xaa Pro Xaa
1

<210> SEQ ID NO 25
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Lys or Arg
<220> FEATURE:
<221> NAME/KEY: MISC_FEATURE
<222> LOCATION: (2)..(3)
<223> OTHER INFORMATION: X at positions 2 and 3 is any amino acid
<220> FEATURE:
<221> NAME/KEY: MISC_FEATURE
<222> LOCATION: (5)..(5)
<223> OTHER INFORMATION: X at position 5 is Val or Ile

<400> SEQUENCE: 25

Xaa Xaa Xaa Ser Xaa
1               5

<210> SEQ ID NO 26
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Ser or Thr
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is Lys or Arg

<400> SEQUENCE: 26

Xaa Xaa Xaa
1

<210> SEQ ID NO 27
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Lys or Arg
<220> FEATURE:
<221> NAME/KEY: MISC_FEATURE
<222> LOCATION: (2)..(3)
```

-continued

```
<223> OTHER INFORMATION: X at positions 2 and 3 is any amino acid
<220> FEATURE:
<221> NAME/KEY: MISC_FEATURE
<222> LOCATION: (4)..(4)
<223> OTHER INFORMATION: X at position 4 is Ser or Thr

<400> SEQUENCE: 27

Xaa Xaa Xaa Xaa
1

<210> SEQ ID NO 28
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Lys or Arg
<220> FEATURE:
<221> NAME/KEY: MISC_FEATURE
<222> LOCATION: (2)..(3)
<223> OTHER INFORMATION: X at positions 2 and 3 are any amino acid
<220> FEATURE:
<221> NAME/KEY: MISC_FEATURE
<222> LOCATION: (4)..(4)
<223> OTHER INFORMATION: X at position 4 is Ser or Thr
<220> FEATURE:
<221> NAME/KEY: MISC_FEATURE
<222> LOCATION: (5)..(5)
<223> OTHER INFORMATION: X at position 5 is any amino acid
<220> FEATURE:
<221> NAME/KEY: MISC_FEATURE
<222> LOCATION: (6)..(6)
<223> OTHER INFORMATION: X at position 6 is Lys or Arg

<400> SEQUENCE: 28

Xaa Xaa Xaa Xaa Xaa Xaa
1               5

<210> SEQ ID NO 29
<211> LENGTH: 3
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is Lys or Arg
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is Ser or Thr

<400> SEQUENCE: 29

Xaa Xaa Xaa
1

<210> SEQ ID NO 30
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
```

<223> OTHER INFORMATION: X at position 1 is Lys or Arg
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is Ser or Thr
<220> FEATURE:
<221> NAME/KEY: MISC_FEATURE
<222> LOCATION: (4)..(4)
<223> OTHER INFORMATION: X at position 4 is any amino acid
<220> FEATURE:
<221> NAME/KEY: MISC_FEATURE
<222> LOCATION: (5)..(5)
<223> OTHER INFORMATION: X at position 5 is Lys or Arg

<400> SEQUENCE: 30

Xaa Xaa Xaa Xaa Xaa
1               5

<210> SEQ ID NO 31
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is any amino acid
<220> FEATURE:
<221> NAME/KEY: MISC_FEATURE
<222> LOCATION: (2)..(2)
<223> OTHER INFORMATION: X at position 2 is Glu or Asp
<220> FEATURE:
<221> NAME/KEY: MISC_FEATURE
<222> LOCATION: (4)..(4)
<223> OTHER INFORMATION: X at position 4 is any amino acid

<400> SEQUENCE: 31

Xaa Xaa Tyr Xaa
1

<210> SEQ ID NO 32
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X at position 1 is any amino acid
<220> FEATURE:
<221> NAME/KEY: MISC_FEATURE
<222> LOCATION: (2)..(2)
<223> OTHER INFORMATION: X at position 2 is Glu or Asp
<220> FEATURE:
<221> NAME/KEY: MISC_FEATURE
<222> LOCATION: (4)..(4)
<223> OTHER INFORMATION: X at position 4 is Ile or Leu or Val

<400> SEQUENCE: 32

Xaa Xaa Tyr Xaa
1

<210> SEQ ID NO 33
<211> LENGTH: 1
<212> TYPE: PRT
<213> ORGANISM: Artificial Sequence
<220> FEATURE:

```
-continued

<223> OTHER INFORMATION: synthetic peptide
<220> FEATURE:
<221> NAME/KEY: MISC_FEATURE
<222> LOCATION: (1)..(1)
<223> OTHER INFORMATION: Y at position 1 is phosphorylated

<400> SEQUENCE: 33

Tyr
1

<210> SEQ ID NO 34
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Y at position 3 is phosphorylated
<220> FEATURE:
<221> NAME/KEY: MISC_FEATURE
<222> LOCATION: (5)..(5)
<223> OTHER INFORMATION: X at position 5 is any amino acid

<400> SEQUENCE: 34

Ala Ala Tyr Ala Xaa Ala Ala
1               5
```

METHODS AND KITS FOR TRANSFERASES

FIELD OF THE INVENTION

The invention relates to enzyme assays. More specifically, the invention relates to the detection of transferase activity, such as kinase activity and phosphatase activity. Furthermore, the invention relates to a process for screening potential inhibitors, activators, and other modifiers of transferases, such as kinases and phosphatases. Moreover, the invention is directed to kits for that can be used for detecting enzymatic activity of transferases, such as kinases and phosphatases, and for detecting inhibitors and activators of transferases.

DESCRIPTION OF THE RELATED ART

Enzymes are classified into groups according to the general kind of reaction they catalyze. Transferases catalyze the transfer of a group from one substrate to another and include kinases and phosphatases. Protein kinases transfer a phosphomoiety from a donor such as adenosine triphosphate (ATP) or guanosine triphosphate (GTP) to an acceptor such as a peptide or protein to yield a phosphorylated peptide or protein and adenosine diphosphate (ADP) or guanosine diphosphate (GDP), respectively. Protein phosphatases are enzymes that transfer a phosphate group from a phosphopeptide or a phosphoprotein donor to an acceptor such as water.

About two to five percent of the eukaryotic genome encodes for protein kinases and protein phosphatases. Although approximately 870 different protein kinases have been identified in the human genome, there may be many thousands of distinct and separate enzymes. In addition, protein substrates for these enzymes may amount to one-third of all cellular proteins. An understanding of these enzymes and their targets is crucial to understanding cellular regulation and cellular pathology.

Protein kinases are often divided into two major groups based on the amino acid residue that is phosphorylated. The first group is serine/threonine kinases, which includes cyclic AMP-dependent protein kinases (PKA), cyclic GMP-dependent protein kinases (PKG), calcium and phospholipid dependent protein kinases (PKC), calcium and calmodulin-dependent protein kinases (CaMK), casein kinases, cell cycle protein kinases (cdc or cdk), protein kinase B (Akt), and others. These kinases are usually cytoplasmic or associated with the particulate fractions of cells, possibly by anchoring proteins. Protein serine/threonine kinases are the most common type of cytosolic kinases, and are thought to be responsible for the majority of phosphorylation events in the cell. In addition, there are some receptor kinases of the serine/threonine type, such as transforming growth factor beta (TGF-β). Overall, serine/threonine kinases represent over 70% of cellular protein kinases.

The second group of kinases, called tyrosine kinases, phosphorylate tyrosine residues. Overall, over 10% of kinases are tyrosine kinases. There are fewer tyrosine kinases, but they play an equally important role in cell regulation. Studies have indicated that many tyrosine kinases are transmembrane proteins with their receptor domains located on the outside of the cell and their kinase domains on the inside of the cell. More than 50 receptor tyrosine kinases are known. These kinases include several receptors for molecules such as growth factors and hormones, cytokines, and neurotransmitters. Examples of these include epidermal growth factor receptor (EGFR), insulin receptor (IR) and platelet derived growth factor receptor (PDGFR). There are also cytosolic tyrosine kinases, such as src, src-N1, fyn, lyk, lynA, lck. In addition, other kinases phosphorylate proteins or peptides containing histidine or aspartic acid residues.

Protein phosphatases are enzymes that catalyze the removal of phosphate moieties from proteins or peptides that contain such modifications. As with kinases, classes of phosphatases are distinguished by their substrate specificity and dependence on other molecules for activation. Three major classes of phosphatases have been identified. The first class includes type 1 protein phosphatase (protein phosphatase-1 or PP1) and type 2 protein phosphatases (PP2A, PP2B, and PP2C). The second class includes tyrosine phosphatases such as PTP-1B, and YOP-51. Some phosphatases in this class are soluble but others comprise parts of a larger molecule, such as the receptor CD45. The third major class of phosphatases includes dual-specificity protein phosphatases that remove phosphate groups from both phosphoserine/phosphothreonine and phosphotyrosine.

Protein kinases and protein phosphatases play very important roles in many cell functions, including, but not limited to, cellular metabolism, signal transduction, transcriptional regulation, cell motility, cell division, cellular signaling processes, cellular proliferation, cellular differentiation, apoptosis, and secretion. These processes are mediated by phosphorylation or dephosphorylation of enzymes, protein substrates, transcription factors, hormone or growth factor receptors, and other cellular proteins.

In addition, protein kinases and protein phosphatases are involved in mediating the response to naturally occurring toxins and pathogens, which alter the phosphorylation states of proteins. Additionally, protein kinases are related to many epidemiologically relevant oncogenes and tumor suppressor genes.

Notably, there are over 400 human diseases in which kinases are implicated. Examples include neurodegenerative diseases such as amyotrophic lateral sclerosis and Alzheimer's disease. In myotonic dystrophy, a genetic defect in one form of the disorder is characterized by an amplified trinucleotide repeat in the 3' untranslated region of a protein kinase gene on chromosome 19. These modifications may someday elucidate many of the unusual features of the disorder.

Because of this role of kinases and phosphatases in human pathology, modulators of kinases and phosphatases are potential drug targets. Currently, many inhibitors of kinases and phosphatases are available for treating a variety of diseases, while others are being tested for such use. One such inhibitor is Gleevec™ (Imatinib mesylate) (Novartis, Basel, Switzerland), which is a protein tyrosine kinase inhibitor of the Bcr-Abl tyrosine kinase. The abnormal constitutive expression of this tyrosine kinase is created by the "Philadelphia chromosome" abnormality in chronic myelogenous leukemia (CML). Gleevec™ inhibits proliferation and induces apoptosis in Bcr-Abl positive cell lines as well as fresh leukemic cells from Philadelphia chromosome positive CML patients.

Fasudil (Eril® Injection S, Asahi Kasei Corp.) is potent inhibitor of Rho-kinase. Eril® has been approved in Japan for the treatment of cerebral vaspasm and an oral formulation is now is in clinical trials for the treatment of angina.

An exemplary inhibitor of a clinically relevant phosphatase is cyclosporine A (CSA), which is used to prevent and treat ongoing acute rejection of transplanted organs. CSA inhibits the production of interleukin IL-2 by helper T-cells, thereby blocking T cell activation and proliferation (and inhibiting amplification of the immune response). The current model for the mechanism of action of CSA suggests that it blocks a phosphatase called calcineurin (PP2B).

Further, phosphotyrosine phosphatase (PTP-1B) is currently under investigation as a target for the treatment of type II diabetes.

These examples illustrate the importance of modulating kinases and phosphatases for clinically relevant circumstances.

Current types of assays used to measure kinase and phosphatase activity and to detect potential kinase and phosphatase inhibitors and activators include Fluorescence Resonance Energy Transfer (FRET) assays, Fluorescent Polarization (FP) assays, and assays based on radioactivity such as Scintillation Proximity Assay (SPA). FRET assays used to detect kinase activity utilize a protein substrate that has two linked fluorescent molecules. The two molecules are in close proximity, separated by a fixed distance. The energy of an excited electron in one molecule (the donor) is passed to an adjacent molecule (the acceptor) through resonance. The ability of a higher energy donor flourophore to transfer energy directly to a lower energy acceptor molecule causes sensitized fluorescence of the acceptor molecule and simultaneously quenches the donor fluorescence. In this case, the fluorescence of the donor is "quenched" by the proximity to the acceptor and the energy of the donor is transferred to the acceptor in a non-radiative manner. The efficiency of energy transfer is dependent on the distance between the donor and acceptor chromophores according to the Forster equation. In most cases, no FRET is observed at distances greater than 100 angstroms and thus the presence of FRET is a good indicator of close proximity.

In order for FRET to be useful, the fluorescence of the acceptor molecule must be significantly different from the fluorescence of the donor. A useful FRET based protein substrate may include a separation of the two fluorescent molecules via a peptide linker that maintains specificity for an endopeptidase that is capable of cleaving the peptide linker between the two fluorophores. If the peptide is phosphorylated, then the enzyme may not cleave the protein or may cleave it at a reduced rate, keeping the fluorescent molecules in close proximity such that quenching occurs. On the other hand, if the protein is not phosphorylated, then the endopeptidase cleaves the protein substrate, releasing the two fluorescent molecules such that the quenching is alleviated, and the two fluorescent molecules fluoresce independently. The FRET assay requires peptide substrates that must be carefully engineered to meet these requirements. That is, the peptide substrates must contain the enzyme recognition site required for the endopeptidase, the distance between the two fluorophores must be within the range to allow FRET to occur and the fluorescent molecules must be paired in such a way that donor fluorescence is significantly quenched, minimizing background fluorescence from the donor. Furthermore, the fluorescence of the starting material (the "quenched" substrate) must be significantly different from the product (the "released" non-quenched product). These requirements make a FRET based assay cumbersome and costly.

FP assays are based on binding of a high affinity binding reagent, such as an antibody, a chelating agent, or the like, to a fluorescently labeled molecule. For example, an antibody that binds to a phosphorylated fluorescently labeled peptide but not to a non-phosphorylated fluorescently labeled peptide can be used for a kinase assay. When the fluorescent label is excited with plane polarized light, it emits light in the same polarized plane as long as the fluorescent label remains stationary throughout the excited state (duration of the excited state varies with fluorophore, and is 4 nanoseconds for fluoroscein). However, if the excited fluorescent label rotates or tumbles out of the plane of polarization during the excited state, then light is emitted in a different plane from that of the initial excitation state. If polarized light is used to excite the fluorophore, the emission light intensity can be monitored in both the plane parallel to the plane of polarization (the excitation plane) and in the plane perpendicular to the plane of polarization. The degree to which the emission intensity moves from the parallel to the perpendicular plane is related to the mobility of the fluorescently labeled molecule. If the fluorescently labeled molecules are large, such as when they are bound to the binding reagent, the fluorescently labeled molecules move little during the excited state interval, and emitted light remains highly polarized with respect to the excitation plane. If the fluorescently labeled molecules are small, such as when no binding reagent is bound to the fluorescently labeled molecules, the fluorescently labeled molecules rotate or tumble faster, and the resulting emitted light is depolarized relative to the excitation plane. Thus, an FP assay requires a high affinity binding reagent, e.g., an antibody, capable of binding with high specificity to the fluorescently labeled molecule. The time consuming and costly optimization of antibody binding with the specific fluorescently labeled molecules such as peptides is required where antibodies are used. Additionally, with FP assay there is the potential for a phosphorylated protein and other reaction components, e.g., lipids and detergents, to interfere with the polarization.

Kinase assays that use radioactive labels include SPA. In SPA, modified ligand-specific or ligand-capturing molecules are coupled to fluoromicrospheres, which are solid-phase support particles or beads impregnated with substances that emit energy when excited by radioactively labeled molecules. When added to a modified ligand such as radiolabeled phosphopeptide in a mixture with the nonphosphorylated peptide, only the phosphopeptide is captured on a fluoromicrosphere, bringing any bound radiolabeled peptide close enough to allow the radiation energy emitted to activate the fluoromicrosphere and emit light energy. If the concentration of fluoromicrospheres is optimized, only the signal from the radiolabeled ligand bound to the target is detected, eliminating the need for any separation of bound and free ligand. The level of the light energy emitted may be measured in a liquid scintillation counter and is indicative of the extent to which the ligand is bound to the target. However, a SPA requires radiolabeled ligands, which have high disposal costs and possible health risks. In addition, a SPA requires the fluoromicrospheres to settle by gravity or be centrifuged, adding an additional step and time to the assay.

With phosphorylation and dephosphorylation events involved in so many cell functions and diseases, identifying kinase and phosphatase activity is tremendously important. Thus, there is a need for alternative enzyme assays for detecting transferase activity, such as protein kinase and protein phosphatase activity, that do not require large amounts of costly or highly specialized starting materials and that do not require a large amount of time to complete. Additionally, there is a need for alternative assays to identify activators and inhibitors of kinases and phosphatases. In addition, it would also be desirable to provide kits for carrying out such assays.

SUMMARY OF THE INVENTION

The invention, which is defined by the claims set out at the end of this disclosure, is intended to solve at least some of the problems noted above. For example, in one aspect of the invention, a method for detecting transferase activity of a sample is provided. In a preferred embodiment of the method, the sample is contacted with a substrate and at least one of a phosphate group donor and a phosphate group acceptor. The substrate includes a reporter compound and amino acids. A peptidase is added that cleaves a non-phosphorylated peptide substrate at a first rate and a phosphorylated peptide substrate at a second rate. The difference in the two rates is a measure of transferase activity. The output of the reporter compound is then detected.

In a preferred embodiment, the method of detecting transferase activity is used to detect kinase activity. In another preferred embodiment, the method is used to detect phosphatase activity.

Also provided is a method for detecting alteration in a transferase reaction. In a preferred embodiment of the method, a test substance is contacted to a substrate including a reporter compound and amino acids under conditions in which the transferase is active. The substrate is cleaved with a peptidase that cleaves a non-phosphorylated peptide substrate at a first rate and a phosphorylated peptide substrate at a second rate. The output of the reporter compound is then detected.

In a preferred embodiment, the method of detecting alterations in a transferase activity is used to detect alterations in kinase activity. In another preferred embodiment, the method is used to detect alterations in phosphatase activity.

Also provided is a method of detecting transferase activity of a sample. In a preferred embodiment of the method, a substrate having a reporter compound conjugated thereto is provided. A quantity of the substrate is added to a solution containing the sample. The sample is incubated with the substrate under conditions where the sample is active for a time sufficient for transferase activity to take place. A peptidase is added to the solution containing the sample. Output of the reporter compound is then detected.

Peptide substrates for transferases are also provided. In a preferred embodiment, the peptide substrate includes a reporter compound and a first transferase substrate linked to the reporter compound on a first side of the reporter compound.

Kits that can be used in carrying out the above methods are also provided. In a preferred embodiment, the kit includes a substrate that includes a reporter compound, at least one of a phosphate group donor and a phosphate group acceptor, and a buffer that supports enzymatic activity of the transferase. Additionally included is a peptidase that cleaves a non-phosphorylated peptide substrate at first rate and a phosphorylated peptide substrate at a second rate.

The methods described herein are homogeneous, fast, sensitive, simple, and non-radioactive. The methods are convenient and can be used with any instrumentation platform. Reagents required can be designed with relative ease and may be synthesized readily. The methods provide assays with fast development time and low cost.

BRIEF DESCRIPTION OF THE DRAWINGS

Preferred exemplary embodiments of the invention are illustrated in the accompanying drawings, in which like reference numerals represent like parts throughout and in which.

Figure 1:
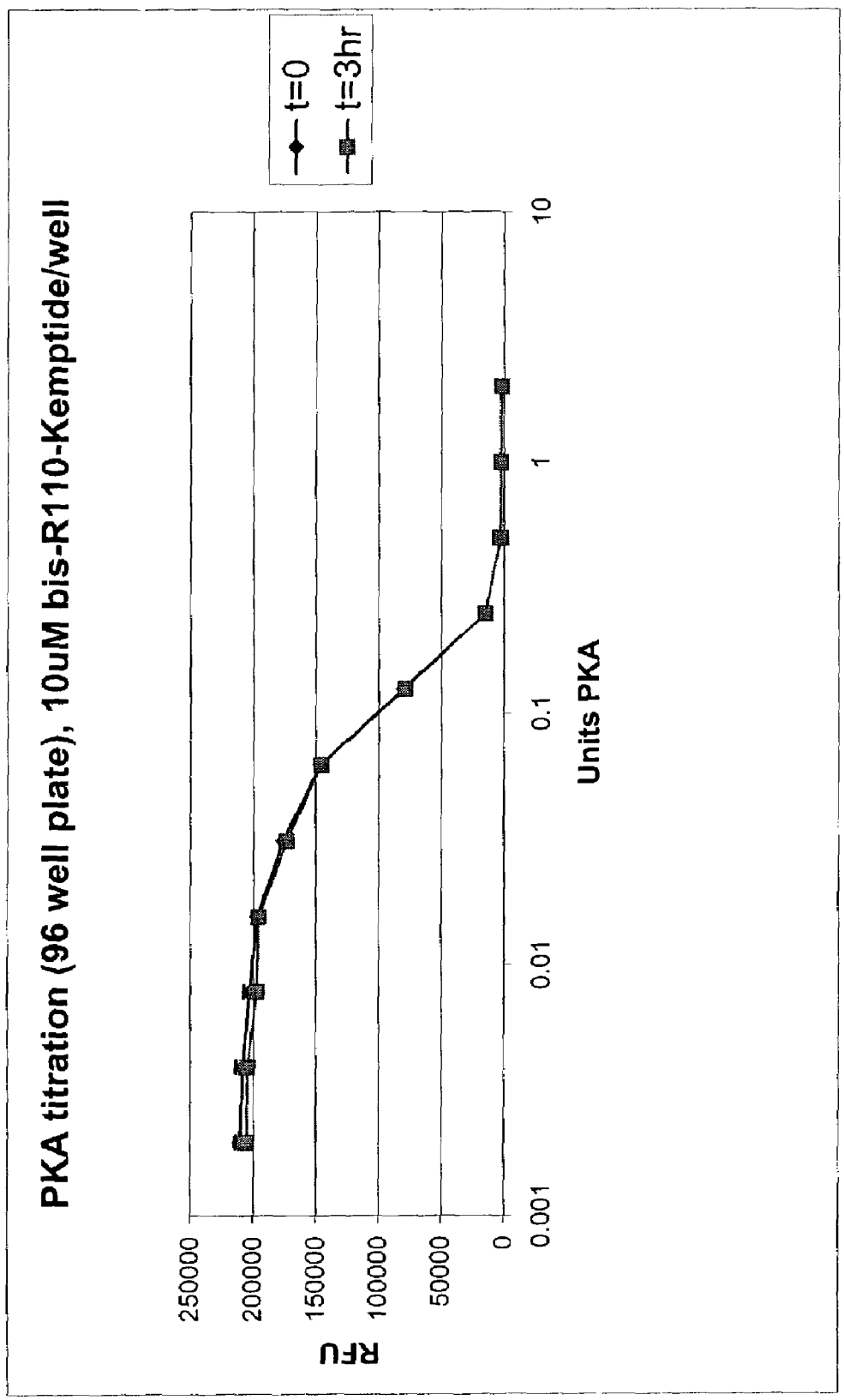
FIG. 1 is a graph showing detected output from a serine/threonine protein kinase assay where the kinase added to the reaction was titrated. Detected output is shown in relative fluorescence units (RFU).

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

Definitions:

For purposes of the present invention, the following definitions apply:

Amino Acid: In keeping with standard polypeptide nomenclature, J. Biol. Chem., 243:3557–59, (1969), abbreviations for amino acid residues are as shown in the following Table of Correspondence:

| TABLE OF CORRESPONDENCE SYMBOL FOR AMINO ACIDS | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |

-continued

TABLE OF CORRESPONDENCE
SYMBOL FOR AMINO ACIDS

| 1-Letter | 3-Letter | AMINO ACID |
|---|---|---|
| K | Lys | lysine |
| H | His | histidine |
| Q | Gln | glutamine |
| E | Glu | glutamic acid |
| W | Try | tryptophan |
| R | Arg | arginine |
| D | Asp | aspartic acid |
| N | Asn | asparagine |
| C | Cys | cysteine |

As used herein, the term "aminoluciferin" refers to luciferin that has been modified to include an $NH_2$ group.

As used herein, the term "background fluorescence" refers to the fluorescence outputted by the reporter compound when it is linked to amino acids of the peptide substrate.

As used herein, the term "bioluminescence" refers to the light produced in certain organisms as a result of luciferase-mediated oxidation reactions. The luciferase genes, e.g., the genes from luminous beetle and, in particular, the luciferase from Photinus pyralis (the common firefly of North America), are currently the most commonly used luminescent reporter genes.

As used herein, the term "dephosphorylation" refers to the removal of a phosphate group.

As used herein, the term "exopeptidase" refers to a hydrolase enzyme that removes terminal amino acids of a peptide or protein by cleaving peptide bonds.

As used herein, the term "luciferase," unless specified otherwise, refers to a naturally occurring or engineered Coleopteran luciferase. The luciferase, if naturally occurring, may be obtained easily by the skilled from the beetle itself, and particularly the light organ thereof. If the luciferase is one that occurs naturally or is engineered, which retains activity in the luciferase-luciferin reaction, of a naturally occurring luciferase, it can be obtained readily from a culture of bacteria, yeast, mammalian cells, insect cells, plant cells, or the like, transformed to express a cDNA encoding the luciferase, or from an in vitro cell-free system for making the luciferase from a nucleic acid encoding same.

As used herein, the term "luciferin" refers to a substrate of a Coleopteran luciferase enzyme. For example, firefly luciferin is a polyheterocyclic organic acid, D-(−)-2-(6'-hydroxy-2'-benzothiazolyl)-$\Delta^2$-thiazoline-4-carboxylic acid.

As used herein, the term "modulator" refers to an agent identified using assays for transferase activity. Samples are treated with a candidate agent. If there is a change in transferase activity between a sample treated with a candidate agent and one not treated with the candidate agent, this change indicates the identification of a modulator. A change in activity can be an increase or decrease.

As used herein, the term "peptide substrate" refers to a peptide that is linked to a reporter compound. Preferably, the peptide substrate includes at least one amino acid linked to at least one side of the reporter compound.

As used herein, the term "peptide" refers to a linear series of at least two amino acid residues connected one to the other by peptide bonds between the alpha-amino and carboxy groups of adjacent residues.

As used herein, the term "phosphorylation" refers to the addition of a phosphate. An amino acid within a peptide that has been phosphorylated is indicated herein with either a "p" that precedes the amino acid or a ($PO_3$) that follows or are otherwise attached to the amino acid.

As used herein, the term "reporter compound" refers to a compound, the output of which can be detected either directly or indirectly. Output can be detected directly where the reporter compound itself has a property that can be detected. Output can be indirectly detected where, e.g., the reporter compound when acted on by another substance produces a property that can be detected.

I. Methods for Assaying Samples for Transferase Activity and for Alterations in Transferase Activity In a preferred embodiment, a method for detecting transferase activity of a sample involves contacting the sample with a substrate and at least one of a phosphate group donor and a phosphate group acceptor. The substrate includes a reporter compound and amino acids, as are explained in detail below. A peptidase is added that cleaves a non-phosphorylated peptide substrate at a first rate and a phosphorylated peptide substrate at a second rate. For example, the peptidase cleaves a non-phosphorylated peptide substrate at a faster rate than a phosphorylated peptide substrate. The output of the reporter compound is then detected. This general assay can be tailored to screen for various transferases, including, but not limited to, kinases and phosphatases. In addition, the general assay can be used to screen for alterations in transferase activity, such as kinases and phosphatases. For instance, the assay can be used to screen for enhancers and inhibitors of transferases (kinases and phosphatases, etc).

In a preferred embodiment, a test substance is contacted to a transferase in the presence of a substrate that includes a reporter compound and amino acids under conditions in which the transferase is active. The substrate is cleaved with an aminopeptidase, which cleaves a non-phosphorylated peptide substrate at a first rate and a phosphorylated peptide substrate at a second rate. The output of the reporter compound is then detected.

In a preferred embodiment, the reporter compound is not linked to a solid support such that a kinase (and phosphatase) reaction and a peptidase reaction can be performed in a solution-phase reaction.

In another preferred embodiment, the peptide substrate is linked to a solid support and the kinase (or phosphatase) reaction and the peptidase reaction are performed in solid phase. Additionally, output is detected in solid phase. The peptide substrate is linked to a solid support via functional groups. A functional group on a peptide substrate should have the ability to bind to another functional group attached to or otherwise part of a solid support. For this, a peptide substrate can be linked to the solid support by incorporating a functional group on the peptide substrate and by having a corresponding functional group on the solid support such that the peptide substrate and the solid support can be linked together.

Examples of useful functional groups include those that contain a carboxy group. Biotin is an example of such a functional group. The carboxy group of the functional group is linked to an amino group on a reporter compound or on a peptide. Streptavidin and avidin are examples of functional groups having amino groups. The amino group of the functional group is linked to a carboxy group on a solid support. Biotin has an affinity for both streptavidin and avidin. Through functional groups, such as biotin and streptavidin, the peptide substrate can be immobilized on a solid support.

The functional group can also be attached to the peptide substrate through other linkages, such as by a thioether (or sulfide) linkage. For example, the peptide substrate includes a free sulfhydryl group and the solid support can be derivatized to contain a maleimide end group (Pierce Biotechnology, Inc., Rockford, Ill.). Other linkages can be used, such as a disulfide linkage. For example, the peptide substrate includes a free sulfhydryl group and the substrate includes a free sulfhydroxy group that oxidizes the free sulfhydryl group of the peptide substrate to form the disulfide linkage. In addition, an amide linkage in which the peptide substrate includes a free carboxy group and a solid support contains an amino group. The free carboxy group can oxidize the free amino group to form an amide linkage between the peptide substrate and the solid support. It should be noted that other types of linkages can also be used and that the location of the functional groups listed above can be reversed. For example, a biotin group can be located on a solid support and a streptavidin or avidin group can be located on the peptide substrate.

In a preferred embodiment, a bis-reporter compound, i.e., a reporter compound having two amino groups, includes a functional group on a first amino group and a peptide on a second amino group. In another preferred embodiment, a bis-reporter compound includes a functional group at a free end of a peptide linked to one of the free amino groups. In yet another preferred embodiment, the peptide substrate includes a functional group on the reporter compound itself. Each of these will now be described in more detail.

In the case of a bis-substituted reporter compound having two free amino groups, the reporter compound is linked via a first amino group to a peptide substrate and a second amino group of the reporter compound is linked to a functional group. For example, a biotin group, which includes a carboxy group, can be linked via an amide bond to the other amino group of the reporter compound. A solid support can then be derivatized to contain streptavidin or avidin derivatives, both of which have affinity (or avidity) for biotin. Additionally, a matrix consisting of avidin or streptavidin or any of their derivatives can be used with a biotinylated reporter compound. Examples of solid supports containing streptavidin include streptavidin linked membranes (SAM®), polystyrene linked avidin, streptavidin plates, streptavidin or avidin coated microtiter plates. For the solid-phase reactions, the kinase (or phosphatase) and peptidase protocols described herein for solution-phase reactions can be followed, and the same detection can be conducted as described earlier for solution-phase assays.

Where two amino groups are present on the reporter compound, a first peptide can be attached to a first amino group and a second peptide can be attached to a second amino group. A functional group can be attached at the free end of the second peptide in any of the manners described above. In this configuration, the peptide attached to the second group and to the functional group acts as a linker and does not serve as a substrate for the peptidase. In addition, the functional group can be linked to the reporter compound through any other suitable linker, e.g., a series of carbons, extending from the free amino group and terminating in, e.g., an amino group. This configuration permits the use of the peptide on the first amino group to act as a substrate in both the kinase (or phosphatase) reaction and in the peptidase reaction.

The reporter can also be linked to the two peptides (or phosphopeptides) of interest on both of its amino groups and also be derivatized on a position of choice on the reporter compound, such as the benzyl group of Rhodamine 110. In a preferred embodiment, the functional group is attached directly to the benzyl group. In another preferred embodiment, the functional group is attached via a linker, such as C6 or C12, that contains, e.g., an amino group. This permits the linkage of the same peptide to the amino groups or different peptides to the amino groups of the reporter compound. Another advantage of having the functional group on a location other than an amino group is that a larger increase in fluorescence is obtained when both amino groups are free, such as by cleavage of peptide attached to the reporter compound. For Rhodamine 110, where one amino group is free, there is a 10-fold increase in fluorescence over where no amino groups are free. For Rhodamine 110, where to amino groups are free, there is a 100-fold increase in fluorescence over where no amino groups are free. Therefore, where the Rhodamine 110 has a function group on a location other than an amino group, this permits both amino groups to be freed, which would result in a 100-fold increase in fluorescence as discussed above. A benefit of having the functional group on a location other than the amino group(s) is that two peptides can be attached to the reporter compound.

II. Methods for Assaying Samples for Protein Kinase Activity a. In General

A preferred embodiment of the invention is an assay to screen for protein kinase activity. Protein kinase activity in a sample can be determined by contacting a sample with a phosphate donor and a peptide substrate for a protein kinase. The peptide substrate includes a reporter compound, amino acids, and a phosphorylation site for a protein kinase.

The peptide substrate is incubated with a peptidase that cleaves a non-phosphorylated peptide substrate at a different rate than it cleaves a phosphorylated peptide substrate. Preferably, peptidase that cleaves a non-phosphorylated peptide substrate at a faster rate than it cleaves a phosphorylated peptide substrate. The output of the reporter compound is then detected. The reporter compound exhibits a different output-property when bound to at least one amino acid of the peptide substrate than when it is not bound to amino acids of the peptide substrate. Where no phosphorylated amino acids are present, the peptidase can cleave the amino acids from the substrate to liberate the reporter compound. When liberated from the peptide substrate, such as through hydrolysis of the surrounding amino acids, the reporter compound has increased output when compared to when it is bound to the peptide substrate. Notably, the presence of a phosphorylated amino acid blocks or slows removal of amino acids by the peptidase. When the reporter compound is linked to amino acids of a peptide substrate, it has no or diminished output. Therefore, the output of the reporter compound can be used to determine whether a peptide substrate is phosphorylated.

The assays of the invention can be performed in a single tube or well. In addition, the assays of the invention are amenable to high throughput screening. For example, the assays can be run in 96 well, 384 well, and plates with even more wells.

A preferred embodiment of the assay to screen for protein kinase activity can be represented schematically with the following equations.

I. Kinase Reaction

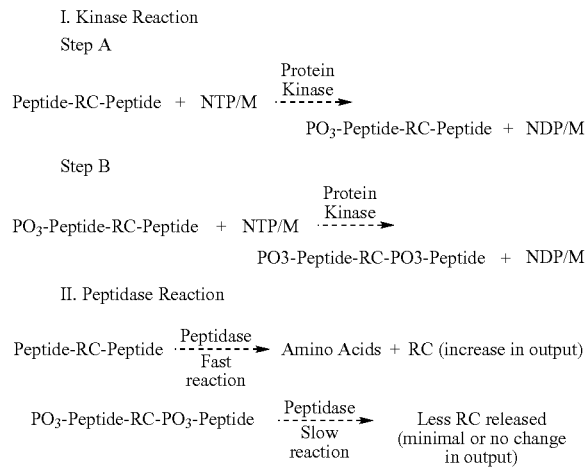

In the equations above, RC is the reporter compound, $PO_3$ is a phosphate group, M is a metal or a divalent cation, and NTP is a nucleotide triphosphate.

b. Kinase Reaction:

In a preferred embodiment, a kinase reaction includes a buffer, a source of metal or divalent cation, a nucleotide triphosphate (NTP), which can act as a phosphate donor, a peptide substrate, and, optionally, an activator of the kinase. The buffer, cation, NTP, and peptide substrate are selected based on the protein kinase under investigation, as is explained below. If desired, an activator of the kinase, can also be added. The sample is added to the reaction.

If the sample contains a protein kinase, the protein kinase can catalyze the transfer of the phosphate group from the NTP to phosphorylate the peptide substrate. Kinase reactions can be incubated at a temperature at which the enzyme is active. Preferably, the temperature is about 21° C. or higher. Also preferred is a temperature of 37° C. or lower. Incubation time preferably is 5 seconds or more. Also preferred is an incubation time of one hour or less. However, the incubation time may be longer than one hour, as long as the reaction time is not longer than the transferase remains active under assay conditions. Incubation time may be optimized depending on, e.g., the incubation temperature, the stability and amount of kinase under investigation, and the amount of peptide substrate. The reaction is instantaneous, so measurement can be taken as soon as is practicable.

Buffers useful in a kinase reaction include, but are not limited to, Tris(hydroxymethyl)aminomethane hydrochloride (Tris-HCl), N-(2-Hydroxyethyl) piperazine-N'-(2-ethanesulfonic acid) (HEPES), 4-(2-Hydroxyethyl)piperazine-1-ethanesulfonic acid) (HEPES), 2-(N-Morpholino) ethanesulfonic acid (MES), at concentrations and pH levels that are optimal for the particular enzyme under investigation. Preferably, the buffer concentration is 10 mM or higher. Also preferred is a buffer concentration of 100 mM or lower. The pH of the kinase reaction preferably is 7.0 or higher. Also preferred is a pH of 9.0 or lower.

A preferred divalent cation for the kinase reaction is magnesium. Other divalent cations, such as manganese, calcium, nickel, and the like, can substitute for magnesium. In addition, these other divalent cations can be combined with magnesium. Notably, some of the other divalent cations can be added for optimal activity of the kinase. Preferably, the divalent cation is added at a 1 mM or higher concentration. Also preferred is adding magnesium at a concentration 50 mM or lower concentration. Other divalent cations can be added in the micromolar to millimolar ranges.

The NTP added to the kinase reaction typically is ATP or GTP. As is known in the art, the choice of which NTP is added to the kinase reaction depends on the kinase used in the assay. A preferred concentration of NTP in a kinase reaction is about 1 uM or higher, and is also preferred at 1 mM or lower, and more preferably is 100 uM.

The peptide substrate for the kinase is one that can be phosphorylated by the kinase. That is, a potential peptide substrate for protein kinase must have an amino acid that can act as a phosphate group acceptor. For example, a peptide substrate for a serine/threonine kinase has a serine or threonine. Consensus sequences for various protein kinases are known. (Methods in Enzymology 200: 62–81 (1991)). Table 1 shows consensus phosphorylation site motifs for various protein kinases. An asterisk indicates the phosphorylable residue. An "X" indicates any amino acid.

TABLE 1

| Protein Kinase | Consensus Motifs |
| --- | --- |
| Calmodulin-dependent protein kinase II | XRXXS*/T* (SEQ. ID. NO:7); XRXXS*/T*V (SEQ. ID. NO:8) |
| Casein kinase I | S(PO₃)XXS*/T* (SEQ. ID. NO:9) |
| Casein kinase II | S*/T*XXEX (SEQ. ID. NO:10); S*/T*XXDX (SEQ. ID. NO:11) |
| c-AMP-dependent protein kinase | RXS* (SEQ. ID. NO:12); RRXS* (SEQ. ID. NO:13); RXXS* (SEQ. ID. NO:14); KRXXS* (SEQ. ID. NO:15) |
| c-GMP-dependent protein kinase | R/KXS*/T* (SEQ. ID. NO: 16); R/KXXS*/T* (SEQ. ID. NO:17); R/KR/KXS*/T* (SEQ. ID. NO:18); R/KXXXS*/T* (SEQ. ID. NO:19); S*/T*XR/K (SEQ. ID. NO:20) |
| Glycogen synthase kinase-3 | S*XXXS(PO₃) (SEQ. ID. NO:21) |
| Growth-associated histone H1 kinase (MPF, cdc2⁺/CDC28 protein kinases) | S*/T*PXK/R (SEQ. ID. NO:22); K/RS*/T*P (SEQ. ID. NO:23); S*/T*PK/R (SEQ. ID. NO:24) |
| Phosphorylase kinase | K/RXXS*V/I (SEQ. ID. NO:25) |
| Protein kinase C | S*/T*XK/R (SEQ. ID. NO:26); K/RXXS*/T* (SEQ. ID. NO:27); K/RXXS*/T*XK/R (SEQ. ID. NO:28); K/RXS*/T* (SEQ. ID. NO:29); K/RXS*/T*XK/R (SEQ. ID. NO:30) |
| Tyrosine kinase/EGF-receptor kinase | XE/DY*X (SEQ. ID. NO:31); XE/DY*I/L/V (SEQ. ID. NO:32) |

The utility of a potential peptide substrate for the assay can be determined by incubating the potential peptide substrate with the kinase under conditions where the kinase is known to be active. Preferred peptide substrates for the kinase assays include a peptide substrate that includes a reporter compound and at least one amino acid and that is useful in a kinase reaction, a reporter compound and at least two amino acids and that is useful in a kinase reaction, and a reporter compound and at least four amino acids and that is useful in a kinase reaction. Those peptide substrates that are useful in a kinase reaction are those that can be phosphorylated by a kinase of interest. Other preferred peptide substrates are listed in the Examples.

The reporter compound in the peptide substrate is any compound that, when released, has a property that is detectably outputted or that is a substrate in a reaction that produces a property that is detectably outputted. For example, when a fluorogenic reporter compound is used, and output is a detectable fluorescence. The fluorogenic reporter compound preferably has no or diminished fluorescence when linked to the amino acids of the peptide substrate. However, when it is liberated from the peptide substrate, the fluorogenic reporter compound has increased fluorescence.

The reporter compound may be a fluorgenic compound, such as aminomethylcoumarin (AMC) or Rhodamine 110 (R-110) or any other fluorogenic compound that can be linked to a peptide without interfering with the recognition site for the kinase or the phosphatase under investigation. Rhodamine 110 is a preferred fluorogenic substrate with a proven utility in high throughput screening applications.

In a preferred embodiment, the reporter compound is covalently linked to the peptide substrate through an amide bond. AMC has a single site at which amino acid chain can be linked, whereas Rhodamine 110 has two. Where Rhodamine 110 is used as a reporter compound, one of the two linkage sites can be blocked with a suitable blocking compound such that only a single site is available for linkage to a peptide. Additionally, where both sites are available on Rhodamine 110, the same peptide can be linked thereto or different peptides can be linked thereto. Where different peptides are used, two different kinases can be assayed using the same modified peptide substrate.

In another preferred embodiment, the reporter compound is a luminogenic compound that when bound to a peptide substrate is not a substrate for a bioluminescent enzyme. Examples include aminoluciferin or any other derivatives of luciferin. For example, when aminoluciferin is enzymatically released from a peptide substrate, it is available as a substrate for luciferase. Luciferase is a bioluminescent enzyme that catalyzes the production of light in the reaction between aminoluciferin and ATP. This resulting light or luminescence produced is the detectable output when such a luminogenic compound is used.

Preferably, the peptide substrate is added at micromolar concentrations, such as at a concentration of at least 1 uM. Also preferred is adding the peptide substrate at a concentration of 25 uM or less.

Activators can be added to the kinase reaction where desired, e.g., where the kinase under investigation requires an activator. It also may be desirable to add an activator to achieve optimal kinase activity. Activators useful in the kinase reaction include, but are not limited to, calcium, phospholipids and other lipids, and phorbol 12-myristate 13-acetate (PMA) or similar activators for Calcium-phospholipid-dependent protein kinase (PKC), calcium and calmodulin for calmodulin-dependent protein kinase (CaM K), cAMP for cAMP-dependent protein kinase (PKA) holoenzyme, cGMP for cGMP-dependent protein kinase (PKG), DNA for DNA-PK. Activators can be added at nanomolar or higher concentrations and at micromolar or lower concentrations depending on the kinase under investigation. A termination reagent can optionally be added to the system in which the kinase reaction is occurring where an end point is desired, e.g., for measuring and quantitating the activity of protein kinase. The termination reagent usually is a metal chelating reagent added at a concentration that is sufficient to sequester the metal away from the kinase. In addition, any other reagent that terminates the phosphorylation catalyzed by the kinase can be used to terminate the phosphorylation reaction. For example, EDTA, EGTA, and 1,10-phenanthroline are good chelators for magnesium, calcium, and zinc, respectively. Other ion chelating agents may be used. Additionally, kinases can be heat inactivated.

The kinase reaction can also be performed using a phosphopeptide as the phosphate donor and a nucleoside diphosphate (NDP) as the phosphate acceptor, i.e., the reverse of the previously described reaction. In this configuration, the kinase reaction is performed in the same manner as is described above. However, the output that is detected generally will be the inverse of the output for kinase reactions where a phosphopeptide is the phosphate donor. That is, where there is kinase activity in this assay configuration, output will increase when dephosphorylation of the phosphopeptide substrate and phosphorylation of the NDP occur.

c. Peptidase Reaction:

A peptidase that is a hydrolase that acts on amide bonds of the peptide substrate is added to the peptide substrate. Peptidases that are particularly useful in the invention include those that are free or substantially free of endopeptidase activity. In addition, it is preferred to have a peptidase that cleaves a non-phosphorylated peptide substrate at a first rate and cleaves a phosphorylated peptide substrate at a second rate. For example, a preferred peptidase shows relatively higher activity when cleaving an amide bond that links an amino acid that has not been modified by phosphorylation than it does cleaving an amide bond that links an amino acid that has been modified by phosphorylation. This difference in the ratio of fluorescence generated from the non-phosphorylated peptides treated with protease compared to that for the phosphorylated peptide treated with the same concentration of protease can be used as in an indicator for the kinase, and permits determination of whether a peptide substrate is phosphorylated. A preferred peptidase is one that hydrolyzes nonphosphorylated amino acids of a peptide substrate sequentially and then dramatically slows hydrolysis when a phosphorylated amino acid is reached. This slowing of hydrolysis results in the failure of the reporter compound to be released in the majority of the molecules of the phosphorylated amino acid. This results in background fluorescence, or significantly lower fluorescence than when a nonphosphorylated amino acid is present. The partial hydrolysis of a phosphorylated amino acid is illustrated schematically below.

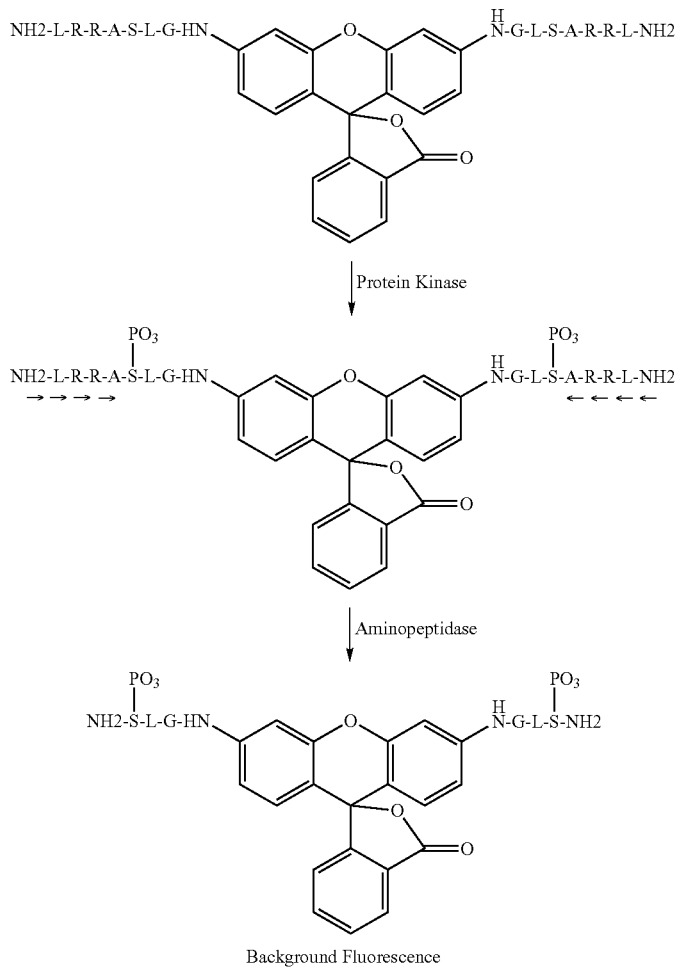

Background Fluorescence

In a preferred embodiment, the increase in activity of the kinase enzyme is proportional to the decrease in detectable output with increasing concentration of enzyme. Conversely, the activity of the phosphatase enzyme is proportional to the increase in output, e.g., fluorescence reading, when compared with the output, e.g., fluorescence, recorded with increasing concentration of phosphatase.

For a nonphosphorlyated peptide substrate, peptidase activity has one rate. For a phosphorylated peptide substrate, peptidase activity has a second rate. For example, for a given enzyme/substrate pair and treatment with aminopeptidase M, the output, e.g., fluorescent units, is higher r for a nonphosphorylated peptide substrate than it is for the phosphorylated peptide substrate.

Preferably, the peptidase is an exopeptidase, which hydrolyzes amino acids starting at a terminus of the peptide substrate. In one preferred embodiment, the peptidase is an aminopeptidase that cleaves a peptide from an amino terminus of a peptide. Where an aminopeptidase is used, the peptide substrate has its carboxy terminus linked to the reporter compound such that the amino terminus of the peptide is free. The peptide substrate used with an aminopeptidase can be represented as $NH_2$-peptide-CO-[reporter compound]-CO-peptide-$NH_2$. Unless otherwise indicated, when peptide substrates that are used with an aminopeptidase are listed herein, it should be understood that the peptide substrate has this configuration.

Aminopeptidases catalyze the release of an N-terminal amino acid, X-l-Y from a peptide, amide, or arylamide, where X may be most amino acids including Pro, although rates of hydrolysis vary. When a terminal hydrophobic residue is followed by a prolyl residue, the two may be released as an intact X-Pro dipeptide. For a nonphosphorylated peptide substrate, the aminopeptidase sequentially cleaves amino acids off the amino terminus of the peptide substrate to free the reporter compound. In addition, a dipeptidyl peptidase, which cleaves peptides from an amino terminus of a peptide, can be used.

Preferred aminopeptidases include Aminopeptidase M (E.C. 3.4.11.2), and aminopeptidase II. Aminopeptidase M is a membrane aminopeptidase. Other names for aminopeptidase M, include, but are not limited to, membrane alanyl aminopeptidase, microsomal aminopeptidase, aminopeptidase N, particle-bound aminopeptidase, amino-oligopeptidase, alanine aminopeptidase, particle-bound aminopeptidase, membrane aminopeptidase I, pseudo leucine aminopeptidase, CD13, Cys-Gly dipeptidase, and peptidase E.

Aminopeptidase II is a peptidase isolated from *Aspergillus oryzae* strain (ATCC20386), is a metalloenzyme, and is a non-specific aminopeptidase (EC 3.4.11). Although the enzyme is capable of cleaving almost any peptide bond, cleaving acidic, basic neutral, hydrophobic or hydrophilic residues, the enzyme is less active with proline when it is present as the penultimate N-terminal amino acid. Any other peptidase that cleaves a nonphosphorylated peptide substrate at a relatively different rate than a phosphorylated peptide substrate and that is free or substantially free of endopeptidase activity can be used for the invention.

Notably, the peptidase can be added to the completed kinase reaction without changing buffers, removing any component of the kinase reaction, or any other step. Therefore, the screening assay can be accomplished in a single tube or well. Preferably, at least 6.5 milliunits of the aminopeptidase is added. Also preferred is adding 100 milliunits or less of the aminopeptidase. A unit of aminopeptidase is defined as the amount of enzyme that will hydrolyze 1 micromole of Leu-pNA per minute at 37° C. and pH 7.0–7.5. Lower and higher amounts of peptidase can be used depending on, e.g., peptide substrate concentration and reaction time for peptide cleavage. The peptidase reaction can be performed at any temperature at which the enzyme is active. Preferably, the peptidase reaction is incubated at a temperature of at least 10° C. Also preferred is a temperature of less than 40° C. Preferably, the peptidase reaction is carried out for 5 seconds or more. Also preferred is carrying out the reaction for 180 minutes or less. Longer reaction times can be used depending, e.g., on the enzyme and peptide substrate concentrations. Shorter reaction times can be used, e.g., with lower peptide substrate concentrations and higher units of aminopeptidase.

The peptidase can also be a carboxypeptidase, which cleaves the carboxy-terminal amino acid from a peptide. The carboxypeptidases that can be utilized include, but are not limited to, carboxypeptidase A, which will remove any amino acid, and carboxypeptidase B, which is specific for a terminal lysine or arginine. Where a carboxypeptidase is used, the peptide substrate has the amino-terminal of a peptide linked to the reporter compound such that the carboxy terminus of the peptide is free. The peptide substrate used with a carboxypeptidase can be represented as COOH-peptide-NH-[reporter compound]-NH -peptide-COOH. Unless otherwise indicated, when peptide substrates that are used with a carboxypeptidase are listed herein, it should be understood that the peptide substrate has this configuration.

If desired, a terminator of the peptidase is included. Exemplary activators include, but are not limited to, actinonin, bestatin, and amastatin. Inclusion of a peptidase terminator is particularly useful where the detection or reading of output is performed at a time later than the ending of the peptidase reaction. Other reagents such as zinc chelators, e.g., 1,10-phenanthroline, can also be used. Peptidase terminators can be added in the micromolar or greater concentrations. Peptidase terminators can also be added in the millimolar or lesser concentrations.

d. Detecting Output

The output of the reporter compound used is detected after the peptidase treatment of the peptide substrate. Where a fluorogenic reporter compound is used, fluorescence can be used as the output. Fluorometery can be used to detect fluorescence. Fluorometers that are single-tube instruments or those that are multi-well plate fluorescence readers can be used to detect fluorescence. For example, the Fluorolog-2 spectrofluometer (SPEX Industries, Inc., Edison, N.J.) equipped with quartz cuvettes can be used for single tube assays. The Cytofluor® II multiwell Fluorescence Plate Reader (PerSeptive Biosystems, Inc., Framingham, Mass.) and the Fluoroscan Ascent CF (LabSystems OY, Helsinki, Finland), both equipped with the appropriate filters, can be used to detect fluorescence. The fluorescence units or readings can be recorded. Where Rhodamine 110 is used as the reporter compound, after peptidase treatment, the kinase reactions preferably are read by exciting at 485 nm and reading emissions at 520 to 530 nm. Where AMC is used, reactions preferably are read by exciting at 360 nm and reading emissions at 420 nm.

Where a luminogenic reporter compound is used, luminescence can be used as output. A luminometer apparatus or other suitable apparatus (such as the Vector 1420 multiwell counter, Wallac Oy, Perkin Elmer, Turku, Finland) can be used to detect the resulting luminescence from the peptidase treatment.

Typical output from a kinase assay is illustrated in FIG. 1, which shows higher fluorescence where less kinase is added and lower fluorescence units where more kinase is added. The shape of the titration curve can be explained by the kinase phosphorylating the peptide substrate such that the ability of the aminopeptidase to cleave the peptide substrate and release the reporter compound is reduced as the concentration of the kinase present increases.

In a preferred embodiment, relative output is determined by comparing the output of a non-phosphorylated peptide substrate to that of a phosphorylated peptide substrate where both peptides have been treated with the same concentration of peptidase. For example, the assay can use the change in relative fluorescence where a fluorogenic compound is used or the change in relative luminescence where a lumogenic compound is used. Relative change in the detectable output of the reporter compound preferably is a ratio of a test sample output to a control sample output. This ratio can be expressed as the relative fluorescence units (RFU). For example, output ratio can be calculated for a sample treated with a kinase and a sample not treated with a kinase.

III. Methods for Assaying for Phosphatase Activity

Another preferred embodiment of the invention is an assay to screen for phosphatase activity. In general, screening for phosphatase activity is achieved similar to the screening for kinase activity, with the major exception of using a substrate for a phosphatase, typically a phosphopeptide substrate, instead of a peptide substrate for a kinase. Other differences between the kinase activity assay and the phosphatase activity assay are described below and in the examples that follow.

In a preferred embodiment for detecting phosphatase activity of a sample, the sample is contacted with a phosphopeptide substrate and a phosphate acceptor. The peptide substrate includes a reporter compound, a dephosphorylation site for a phosphatase, and amino acids. A potential peptide substrate for protein phosphatase must have a phosphoamino acid that can act as a phosphate group donor. For example, a peptide substrate for a serine/threonine phosphatase has a phosphorylated serine/threonine and a peptide substrate for a tyrosine phosphatase has a phosphorylated tyrosine. The phosphopeptide substrate is linked to the reporter compound, as defined above.

In a preferred embodiment for detecting phosphatase activity of a sample, the sample is contacted with a phosphopeptide substrate and a phosphate acceptor. The peptide substrate includes a reporter compound, a dephosphorylation site for a phosphatase, and amino acids. A potential peptide substrate for protein phosphatase must have a phosphoamino acid that can act as a phosphate group donor. For example, a peptide substrate for a serine/threonine phosphatase has a phosphorylated serine/threonine and a peptide substrate for a tyrosine phosphatase has a phosphorylated tyrosine. The utility of a potential peptide substrate for the assay can be determined by incubating the potential phosphopeptide substrate with the enzyme under conditions where the enzyme is known to be active. The phosphopeptide substrate is linked to the reporter compound, as defined above.

Although phosphatase substrate preferences are less stringent than kinase substrate preferences, various protein phosphatases indeed have known substrate preferences. (see, e.g., Eur. J. Biochem 219:109–117 (1994)). For example, for phosphatase-2B (PP-2B), which belongs to the family of Ser/Thr-specific enzymes but also is active on phosphotyrosine residues, is believed that higher-order structure is an important determinant for its substrate specificity. However, a number of shorter peptides are also appreciably dephosphorylated by PP-2B, their efficiency as substrates depending on local structural features. For instance, all the peptides that are appreciably dephosphorylated by PP-2B contain basic residue(s) on the amino-terminal side. A basic residue located at position-3 relative to the phosphorylated residue plays a particularly relevant positive role in determining the dephosphorylation of short phosphopeptides. Acidic residue(s) adjacent to the carboxy-terminal side of the phosphoamino acid are conversely powerful negative determinants, preventing the dephosphorylation of otherwise suitable peptide substrates. However, PP-2B displays an only moderate preference for phosphothreonyl peptides, which are conversely strikingly preferred over their phosphoseryl counterparts by the other classes of Ser/Thr-specific protein phosphatases. Moreover PP-2B does not perceive as a strong negative determinant the motif Ser/Thr-Pro in peptides where this motif prevents dephosphorylation by the other classes of Ser/Thr protein phosphatases. Whenever tested on phosphotyrosyl peptides, PP-2B exhibits a specificity that is strikingly different from that of T-cell protein tyrosine phosphatase, a bona fide protein tyrosine phosphatase. In particular, while the latter enzyme is especially active toward a number of phosphopeptides reproducing the phosphoacceptor sites of src products and of PP-2B whose amino-terminal moieties are predominantly acidic, the artificial substrate phospho-angiotensin II, bearing an arginine residue at position-2, is far preferred by PP-2B over all phosphotyrosyl peptides of similar size. Collectively taken, these results show that the specificity of PP-2B, rather than resting on a given consensus sequence, is determined by a variety of primary and higher-order structural features conferring to it an overall selectivity that is different from those of any other known protein phosphatase.

Preferred peptide substrates for the phosphatase assays include a peptide substrate that includes a reporter compound and at least one amino acid and that is useful in a phosphatase reaction, a reporter compound and at least two amino acids and that is useful in a phosphatase reaction, and a reporter compound and at least four amino acids and that is useful in a phosphatase reaction. Those peptide substrates that are useful in a phosphatase reaction are those that can be dephosphorylated by a phosphatase of interest. Preferred peptide substrates include $Y(PO_3)$ (SEQ. ID. NO:33)—Reporter Compound—$Y(PO_3)$, where reporter compound is any reporter compound; $Y(PO_3)$—R-110-$Y(PO_3)$; and AAY$(PO_3)$AXAA (SEQ. ID. NO:34)-R-110-AAXAY$(PO_3)$AA, where X is any amino acid. Other preferred peptide substrates are listed in the Examples.

Added to the phosphatase reaction is a peptidase that cleaves a non-phosphorylated peptide substrate at a faster rate than it cleaves a phosphorylated peptide substrate, as is described in detail above. This permits assessment of dephosphorylation of the phosphopeptide substrate. The detectable output of the reporter compound can be detected, as is described in detail above. Representative output results of a phosphatase activity assay are shown, for example, in FIG. 6.

The protein phosphatase activity assay can be represented schematically with the following equations.

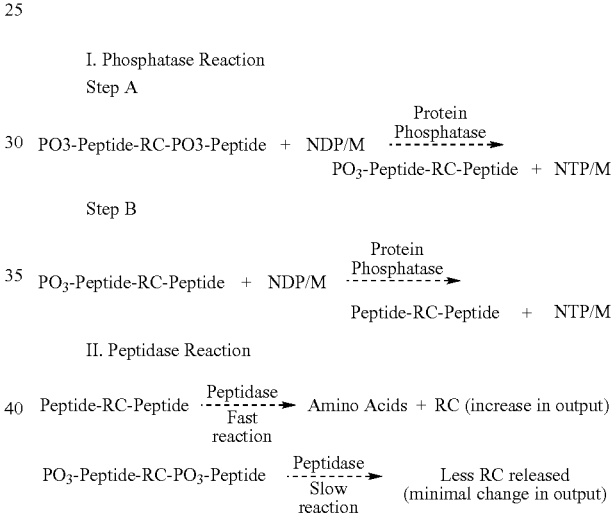

In the above equations, RC is the reporter compound, $PO_3$ is a phosphate group, and M is a metal or a divalent cation.

The de-phosphorylation of a phosphopeptide substrate and hydrolysis thereof is illustrated schematically below.

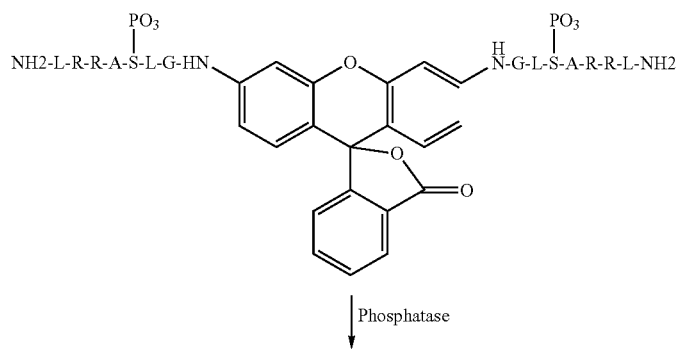

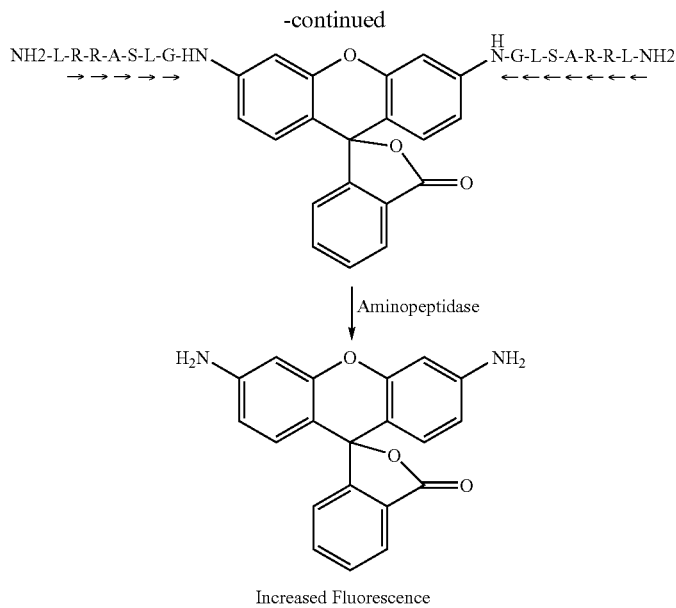

Increased Fluorescence

In a preferred embodiment for a serine/threonine phosphatase, the phosphatase reaction includes a phosphopeptide substrate, buffer, such as Tris-HCl, pH 7.5, bovine serum albumin (BSA), a metal or divalent cation, such as $MgCl_2$ or $MnCl_2$. In addition, as is known in the art, other activators, such as calmodulin, may be added to achieve optimal enzymatic activity. Reactions can be incubated at any temperature at which the phosphatase is active. Preferably, the reactions are incubated at room temperature for 30 minutes.

Where desired, phosphatase reactions can be terminated, such as by adding okadaic acid, EDTA and/or EGTA. After termination (where used), peptidase is added, and the reaction is incubated at 25° C., preferably for at least 60 minutes. Where the reporter compound is a fluorogenic compound, such as Rhodamine 110, fluorescence can be read at an excitation of 480 nm and an emission at 520 nm.

IV. Methods for Screening for Alterations in or to Kinase Activity

A further embodiment of the invention is an assay to screen for alterations in or to a kinase reaction. Alterations include, but are not limited to, activations or inhibitions of a kinase reaction. For this, a test substance that is a potential activator or inhibitor of a kinase is added to the assay along with the kinase. An assay typically includes a buffer, a cation, NTP, peptide substrate, and 0.05 units or greater of the kinase of interest.

The potential inhibitor or activator is added to the reaction to determine whether a compound inhibits or stimulates the phosphorylation reaction. In addition, a peptidase is added to the reaction as detailed above. The potential inhibitor or activator can produce a change in the detectable output from the reporter compound. For example, where a potential inhibitor is included in the assay, typically an increase in the detectable output from the reporter compound indicates inhibition of the kinase. This increase would be due to inhibition of the kinase, leading to reduced phosphorylation of the peptide substrate. With fewer amino acids of the peptide substrate phosphorylated, the peptidase can cleave more molecules of the peptide substrates to liberate more reporter compound than a non-inhibited kinase reaction. Conversely, where a potential enhancer is included in the assay, a decrease in output from the reporter compound when compared to a control reaction without the potential enhancer indicates the enhancement of the kinase.

In a preferred embodiment, output from a test sample contacted with a test substance is compared to output of a control sample that has not been contacted with the test substance. Preferably, a ratio is calculated from these detected outputs. The ratio is a measure of the phosphorylation (or lack thereof) of the reporter compound by the kinase.

V. Methods for Screening for Alterations in or to Phosphatase Activity

An additional embodiment of the invention is an assay to screen for alterations in or to a phosphatase reaction. Alterations include, but are not limited to, activations or inhibitions of a phosphatase reaction. For this, a test substance that is a potential inhibitor of a phosphatase is added to the assay along with the phosphatase. An assay typically includes a buffer, a cation, a phosphopeptide substrate, and 0.1 units or greater of the phosphatase of interest.

The potential inhibitor or activator is added to the reaction to determine whether a compound inhibits or stimulates the dephosphorylation reaction. In addition, a peptidase is added to the reaction as detailed above. The potential inhibitor or activator can produce a change in the detectable output from the reporter compound. For example, where a potential inhibitor is included in the assay, typically a decrease in the detectable output from the reporter compound indicates inhibition of the phosphatase. This decrease would be due to inhibition of the phosphatase, leading to decreased dephosphorylation of the peptide substrate. With more amino acids of the peptide substrate remaining phosphorylated, the peptidase can cleave fewer molecules of the peptide substrate to liberate less reporter compound to a non-inhibited phosphatase reaction. Conversely, where a potential enhancer is included in the assay, an increase in output from the reporter compound when compared to a control reaction without the potential enhancer indicates the enhancement of the phosphatase.

In a preferred embodiment, output from a test sample contacted with a test substance is compared to output of a control sample that has not been contacted with the test substance as is described above.

VI. Kits

The invention also relates to kits for carrying out the methods described above. In a preferred embodiment, the kit includes a substrate that includes a reporter compound, a buffer that supports enzymatic activity of the transferase, at least one of a phosphate donor and a phosphate acceptor, and a peptidase compatible with the substrate. The transferase under investigation may be included in the kit, or may be provided by the user. The transferase can be a kinase, a phosphatase, or another transferase under investigation. Where the transferase is a kinase, the substrate preferably is a peptide substrate that acts as a phosphate group acceptor, and the phosphate donor preferably is an NTP that the kinase is capable of using. Where the transferase is a phosphatase, the substrate preferably is a phosphopeptide substrate that acts as a phosphate group donor. Other components, such as activators of the transferase under investigation, a terminator for the transferase, a terminator for the peptidase, and the like, all of which has been described previously, can also be included. In a preferred embodiment, the kit for screening for transferase activity also optionally includes a transferase that can be used for a control reaction. A kit including a transferase can also be used to determine whether a test substance alters the activity of the transferase. For example, the kit can be used to determine whether a test substance enhances or inhibits the transferase under study.

In one preferred embodiment, the substrate is a kinase substrate. In another preferred embodiment, the substrate is a phosphatase substrate. Preferably, the peptidase of the kit is an aminopeptidase, although it can be another peptidase, such as a carboxypeptidase. Preferred aminopeptidases include, but are not limited to Aminopeptidase M and Aminopeptidase II. A preferred reporter compound for the substrate is a fluorogenic or luminogenic compound, as described above.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Detection of Ser/Thr Kinase using R110-Modified Peptide Substrate and Aminopeptidase M:

PKA Assay With LRRASLG-(R110)-GLSARRL. The kinase activity of the catalytic subunit of cAMP-dependent protein kinase (PKA) from Promega Corp., Madison, Wis. was tested in triplicate in a 96-well plates using the following reaction components: 40 mM Tris-HCl, pH 7.5, 20 mM $MgCl_2$, 0.1 mg/ml bovine serum albumin (BSA), 50 µM ATP, and 5 µM of LRRASLG (SEQ. ID. NO:1)-R110-GLSARRL, a bis-rhodamine peptide kinase substrate also known as "bis-kemptide." The final reaction volume was 50 uL. The amount of PKA added to each reaction was titrated in 2-fold unit increments, in a range from 0.001 unit to 1 unit. Control reactions with 0 units were also run. All kinase reactions were incubated at room temperature for 20 minutes.

The kinase reactions were terminated by adding a termination/detection reagent (25 ul) containing 100 mM EDTA and 25 mU aminopeptidase M (Calbiochem, San Diego, Calif.).

Terminated reactions were incubated at room temperature for 30 minutes, and aminopeptidase activity was then terminated by the addition of a final concentration of 2.5 uM actinonin/well. Enzymatic activity of the kinase was measured by taking a reading of the fluorescence, at the time of addition of actinonin and 3 hrs later to test the stability of the signal, with an excitation at 480 nm and fluorescence emission at 520–530 nm.

As shown in FIG. 1, there is a corresponding decrease in fluorescence output with increasing concentration or units of enzyme in the reaction. In addition, it was also determined that greater units of the catalytic subunit of PKA yielded lower fluorescent output. This can be explained by phosphorylation of the peptide substrate, which decreases the rate of cleavage by Aminopeptidase M to result in decreased release of Rhodamine 110. Moreover, the signal was very stable over time as shown by almost identical profile obtained 3 hrs after termination of aminopeptidase activity.

Other protein kinase sources (e.g., Calzyme Laboratories (San Luis Obispo, Calif.)) were also tested and gave essentially similar results.

Example 2

Inhibition of Ser/Thr Protein Kinases:

PKA Assay With Inhibitors. The effects of various inhibitors of PKA kinase were tested. A known and specific inhibitor of PKA (PKI-"protein kinase inhibitor"), a general and nonspecific inhibitor of PKA (staurosporin ((9S-(9α, 10β,11β, 13α)-2, 3,10,11,12,13-Hexahydro-10-methoxy-9-methyl-11-(methylamino)-epoxy-1H, 9H-diindolo[1,2,3-gh: 3',2',1'-1m]pyrrolo {3,4j]][1,7]benzodiazonin-1-one)), a poor inhibitor of PKA (H7) (1-(5-isoquinolinesulfonyl)-2-methylpiperzine), and a compound that does not inhibit PKA (U0126) (1,4-diamino-2,3-dicyano-1,4-bis-(2-aminophenylthio)butadiene) were tested for their effect on the kinase activity of PKA. Kinase reactions and aminopeptidase reactions were run under conditions similar to those described in Example 1 except that inhibitors were included at increasing concentrations and 0.5 units of PKA was used. A control was included which did not have contain any inhibitor.

Figure 2:
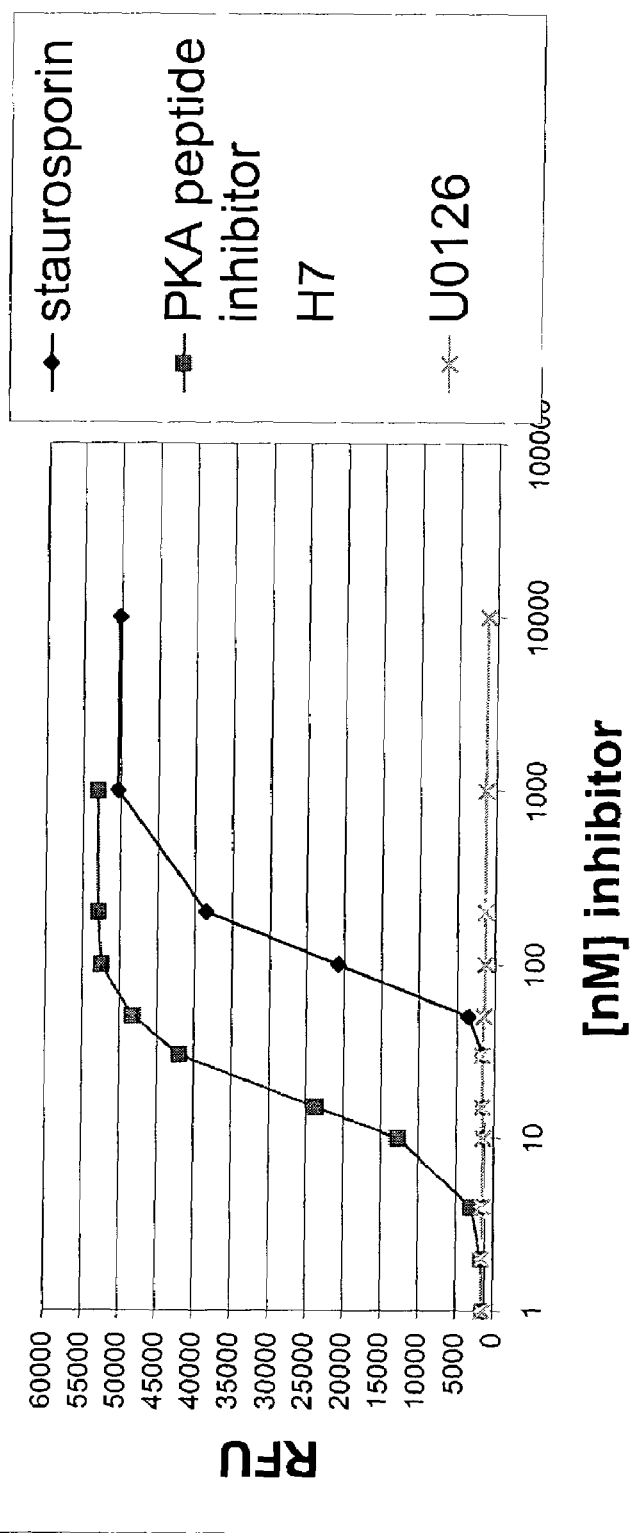
FIG. 2 is a graph showing detected output in RFU from a serine/threonine protein kinase assay in the presence of certain inhibitors.

Fluorescence was detected with an excitation of 480 nm and fluorescence emission at 520–530 nm. As shown in FIG. 2, increasing the concentration of PKI and staurosporin resulted in an increase in fluorescence output indicating inhibition of PKA enzyme activity. The compounds H7 and U0126 were without effect since fluorescence output did not change. It is also apparent the PKI is more a potent inhibitor than staurosporin as lower concentrations of the former was capable of inhibiting 50% of enzyme activity ($IC_{50}$) than the latter (FIG. 2).

Kinase reactions were also run with two additional peptide substrates: Peptide substrate bis-SPK-2 (KKALR-RASLKG (SEQ. ID. NO:2)-R110-GKLSARRLAKK) and bis-SPK-4 (KKALRKASVRG (SEQ. ID. NO:3)-R110-GRVSAKRLAKK) under similar conditions as those listed above. This test demonstrated that the peptide substrate bis-SPK-2 is a better substrate for PKA than the peptide substrate bis-SPK-4. In addition, a monoamide peptide substrate was compared to a bisamide peptide substrate, and similar profiles were obtained, except that the background was higher for the mono substituted Rhodamine 110 compared to the bis-substituted Rhodamine 110 derivative. This property of Rhodamine 110 derivatives is well known in the art (Results not shown).

The reactions were carried out in single tube, 96-well, and 384-well formats, and both white and black plates were used. Black plates were preferred due to their lower reflectivity resulting in lower equipment associated-background. Other serine/threonine protein kinases, such as PKG, PKC, AKT, were also tested using substrate SPK-2, and the change in output fluorescence in each assay was inversely proportional to the amount of enzyme in the reaction (Results not shown).

Example 3

Detection of Ser/Thr Kinase Activity using AMC-Modified Peptide Substrate and Aminopeptidase M:

cAMP-dependent Protein Kinase (PKA) assay with LRRASLG-AMC. Other fluorogenic reporters, such as 7-amino-4-methylcoumarin (AMC), were tested for their suitability for use with PKA. AMC was linked to peptide LRRASLG in an amide bond via a free amino group, producing the peptide substrate kemptide-AMC. This substrate was used under assay conditions that were identical to those used with the Rhodamine 110-modified peptide substrate, except that the substrate was added at a concentration of 40 uM. Reactions were incubated at room temperature for 30 minutes and Aminopeptidase M was added at a final concentration of 50 mU/well and incubated at room temperature for 60 minutes. Reactions were carried out in the presence and absence of 50 uM ATP to show that the phosphotransferase activity of PKA requires ATP. Fluorescent data were obtained at sixty minutes, without addition of actonin. Fluorescence was detected with an excitation of 360 nm and a fluorescence emission at 420 nm.

Figure 3:
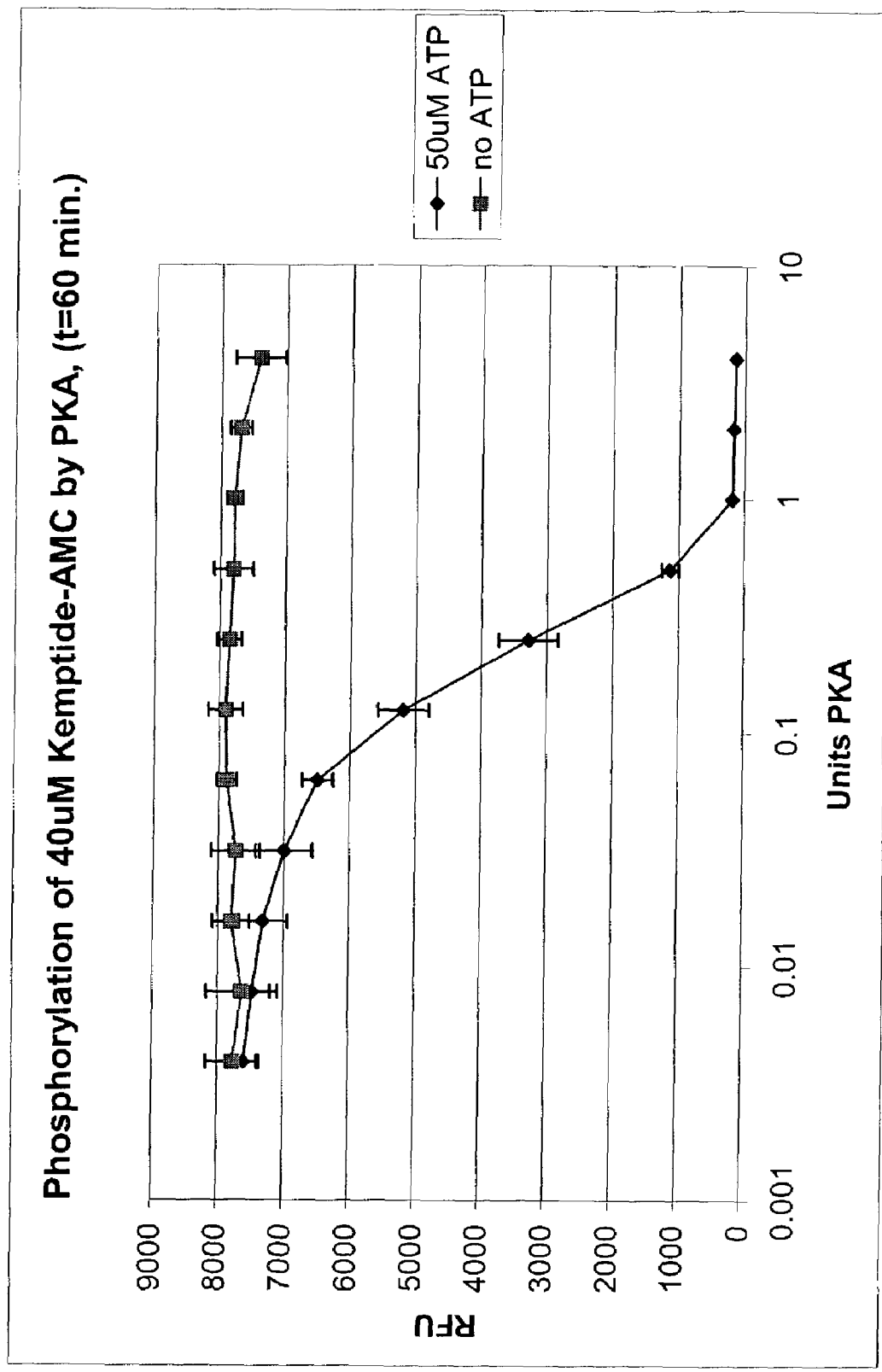
FIG. 3 is a graph showing detected output in RFU from a serine/threonine protein kinase assay using an aminomethyl coumarin labeled peptide substrate.

The results in FIG. 3 show that in the absence of ATP, there is no change in the fluorescence output with increasing enzyme concentrations. In the presence of ATP, the fluorescence output decreased in proportion to the increase in amount of enzyme. These data show that any fluorogenic reporter compound can be used in the invention.

Example 4

Detection of Tyrosine Kinase using R110-Modified Peptide Substrate and Aminopeptidase M:

Tyrosine Kinase Assays. The kinase activity of tyrosine kinases was demonstrated using peptide substrates containing tyrosine as the phosphorylatable amino acid residue. The kinase activity of several enzymes of the Src family of protein tyrosine kinases, such as Fyn, Lyn A, Lyk, Src, Src N1, and for the kinase activity of a growth factor receptor tyrosine kinases (insulin receptor) were tested.

Conditions for the tyrosine kinase reactions include Tris-HCl, pH 7.5, 0.1 mg/ml BSA, 20 mM $MgCl_2$, 1 mM $MnCl_2$, 0.2 mM EGTA, 100 uM sodium vanadate, 8 mM beta glycerophosphate, 2 uM bis-PTK-5 (YIYGAFKRRG (SEQ. ID. NO:4)-R110-GRRKFAGYIY), in a volume of 50 ul/well. Enzyme titrations for the tyrosine kinase 1 ck, were run with 2-fold increments of enzyme from 0.07 mU to 40 mU, as well as a control containing no enzyme. Reactions were carried out with and without 100 uM ATP at room temperature for 30 minutes. Samples were run in Dynex® Microfluor® 2, black, 96-well plates (Dynex Technologies, Inc., Chantilly, Va.).

Figure 4:
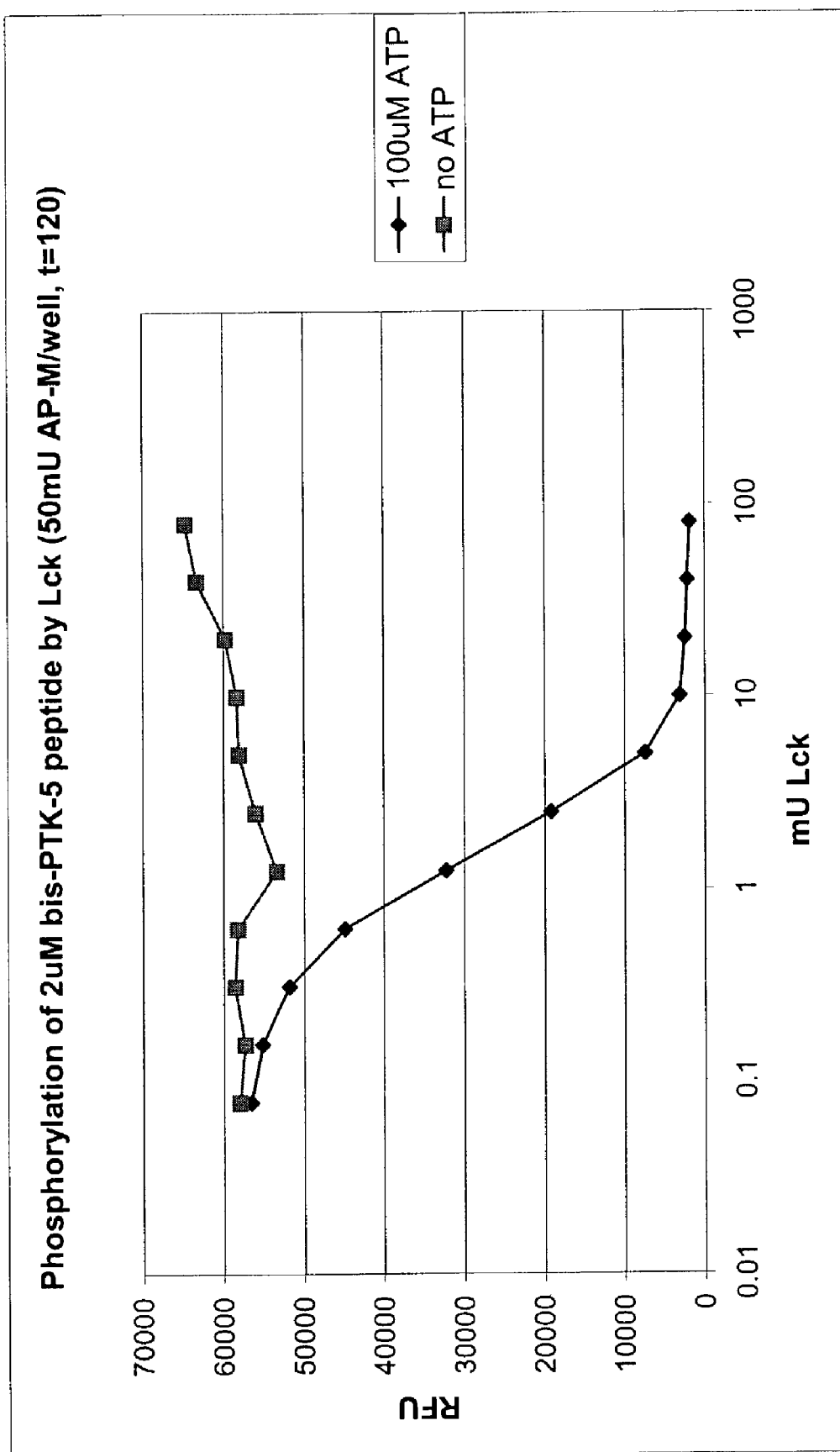
FIG. 4 is a graph showing detected output in RFU from a protein tyrosine kinase assay.

Kinase reactions were terminated by the addition of 25 ul of 100 mM EDTA. Aminopeptidase M (50 mU) was added and incubated at 25° C. for 90 minutes. Fluorescence was then read using an excitation at 480 nm and emission at 520–530 nm, as in Example 1. Results shown in FIG. 4 indicate that where 100 um ATP was included the decrease in fluorescence output was proportional to the increase in amount of enzyme in the reaction, and little or no change was observed in the absence of ATP.

Figure 5:
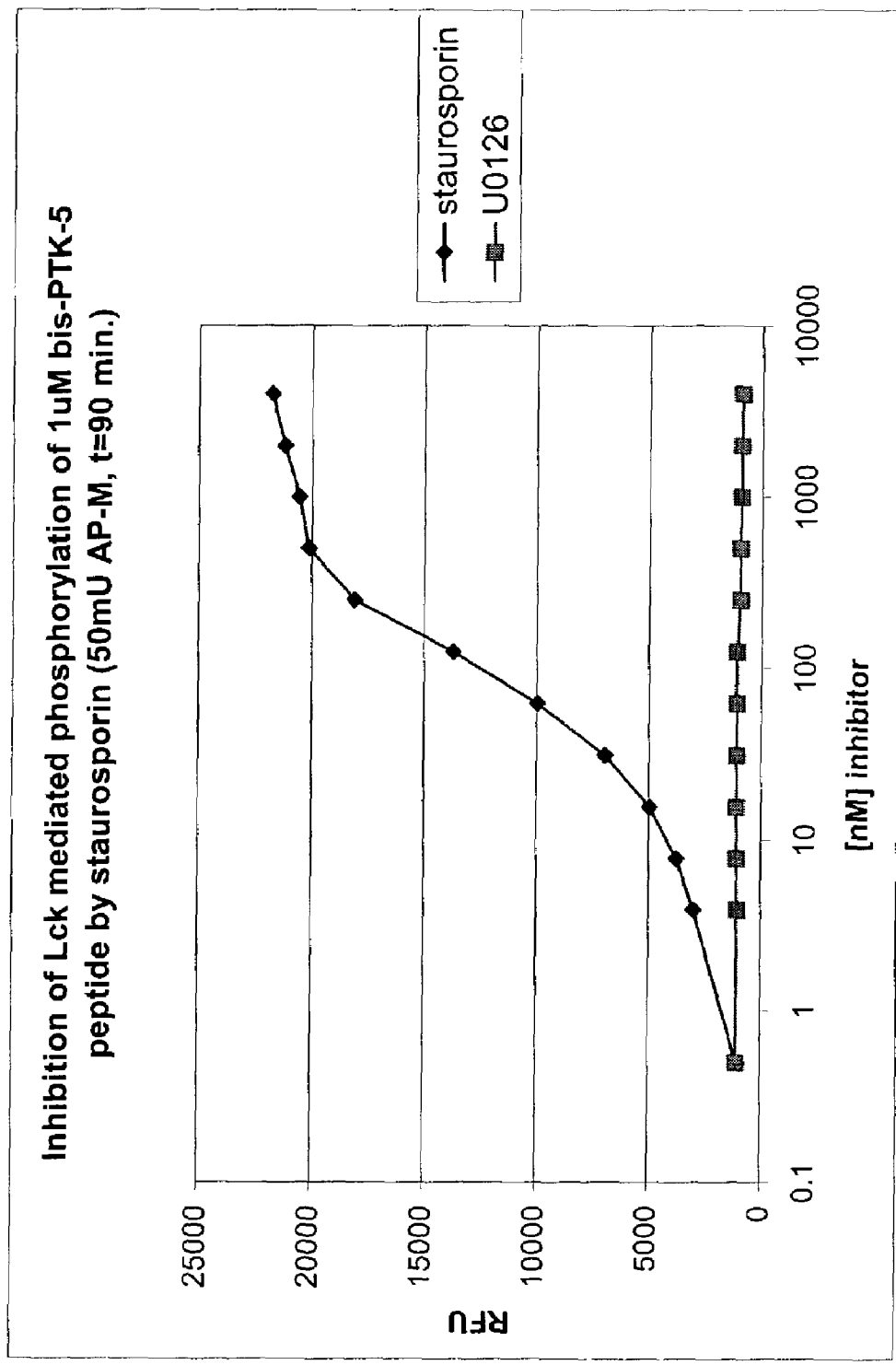
FIG. 5 is a graph showing detected output in RFU from a protein tyrosine protein kinase assay in the presence of certain inhibitors.

In another experiment, it was shown that a nonspecific inhibitor of the tyrosine kinase lck (staurosporin), but not a compound that does not inhibit the kinase (U0126), can reverse the change in fluorescence confirming that the change in fluorescence is attributable to the enzyme activity of 1 ck (FIG. 5).

Example 5

Detection of Ser/Thr Phosphatase Activity using R110-Modified Peptide Substrate and Aminopeptidase M:

PP2A activity with STP-R-110. The phosphatase activity of phosphatase 2A (PP2A) was carried out in 50 ul volume containing 5 uM of phosphopeptide substrate bis-STP-R110 (RRAT($PO_3$)VA (SEQ. ID. NO:5)-R110-AV($PO_3$)TARR), 40 mM Tris-HCl, pH 7.5, and 0.1 mg/ml BSA. Phosphatase reactions were initiated by adding the enzyme serine/threonine phosphatase PP2A from Promega (Madison, Wis.). The amount of PP2A added to each reaction was titrated in ½ increments, in a range from 0.0075 ng (0.015 munits) to 7.5 nanograms (15 munits), plus control reactions containing no enzyme. Phosphatase reactions were carried out for 10 minutes at room temperature in 96-well plates.

Figure 6:
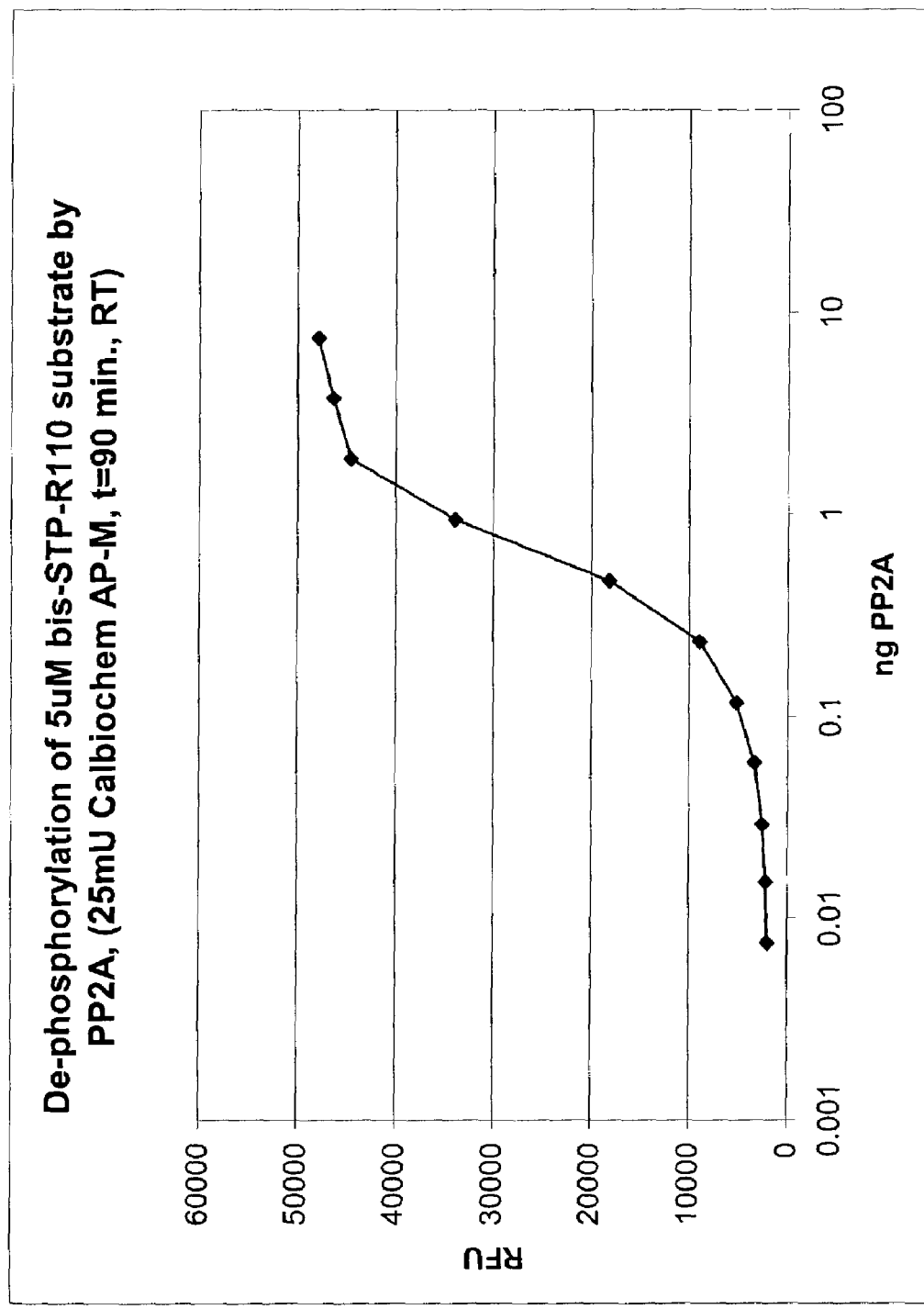
FIG. 6 is a graph showing detected output in RFU from a serine/threonine protein phosphatase assay where the phosphatase added to the reaction was titrated.

Phosphatase reactions were terminated with 25 ul of 2 uM okadaic acid ((9,10-Deepithio-9,10-didehydroacanthifolicin) (sodium salt)), a known inhibitor of PP2A. After termination, 25 mU/well of Aminopeptidase M was added in 40 mM Tris buffer, pH 7.5, 0.1 mg/ml BSA. The aminopeptidase reaction was incubated at room temperature, 25° C., for 90 minutes. Fluorescence was read as in Example 1. The results in FIG. 6 show that PP2A dephosphorylated the substrate efficiently, and fluorescence increased proportionally to the amount of enzyme in the reaction.

Figure 7:
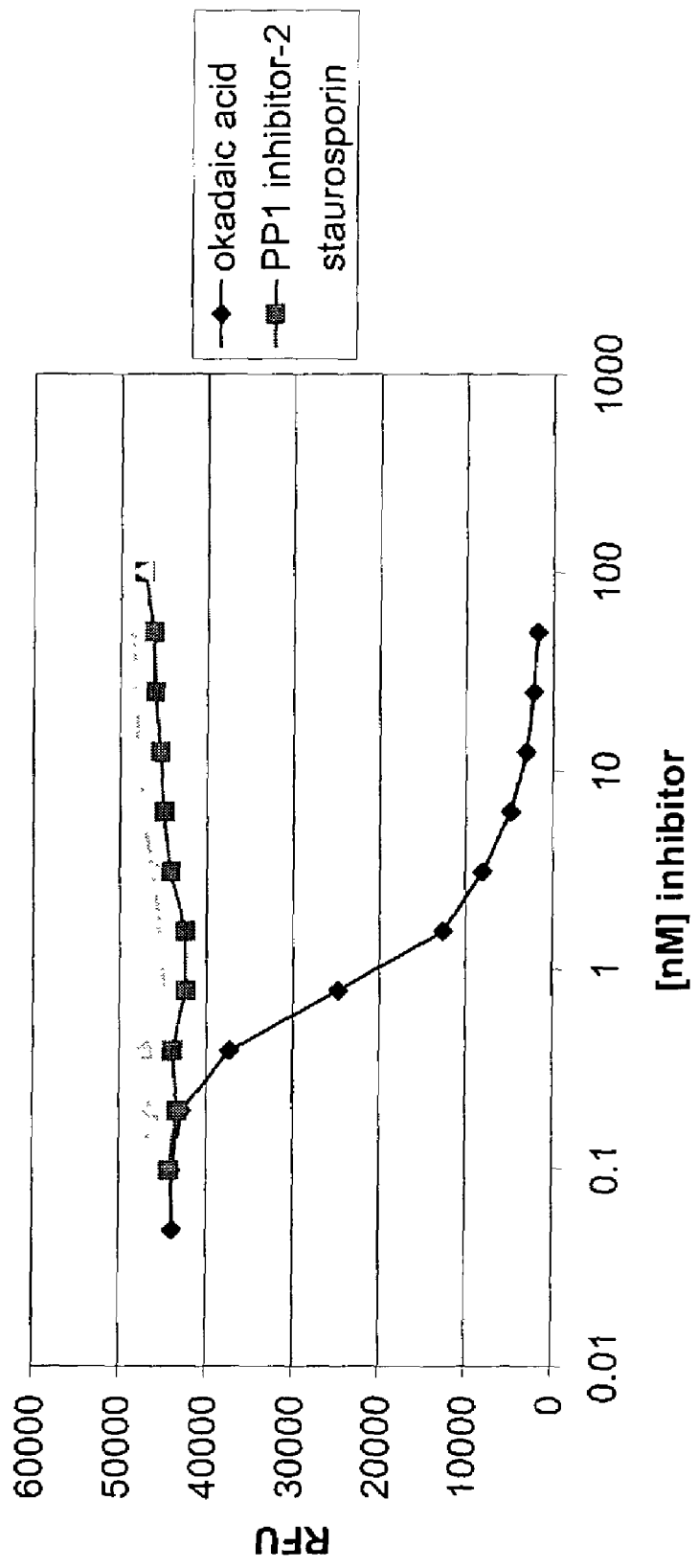
FIG. 7 a graph showing detected output in RFU from a serine/threonine protein phosphatase assay in the presence of certain inhibitors.

The specificity of the phosphatase activity using this substrate was also validated using a specific inhibitor of PP2A (okadaic acid) and with PP1 inhibitor-2, which is known to inhibit PP1 but not PP2A, and staurosporin, which also does not inhibit PP2A. The same assay protocol described herein was used the presence of 2 nanograms of PP2A (4 munits) and 5 uM of the phosphopeptide substrate STP5. Inhibitors were included in the reactions at concentrations ranging from zero inhibitor up to 100 nM. It is clear from FIG. 7 that dephosphorylation of the substrate by PP2A was only inhibited in the presence of increasing concentrations of okadaic acid and not in the presence of PP1 inhibitor-2 or staurosporin, confirming the specificity of assay for PP2A. The concentration of okadaic acid required to inhibit 50% of PP2A activity ($IC_{50}$) was less than 1 nM, which agrees with known values for okadaic acid inhibition of PP2A.

Phosphatase PP2A was also tested in a 384-well format. The reproducibility in the 384 plates was found to be excellent.

Enzyme activity of PP1, PP2B, and PP2C were also tested using the same substrate but with appropriate known cofactors added for each enzyme to obtain optimal enzyme activity in the assay. The results obtained show excellent proportionality between the fluorescence output and dephosphorylation of the substrate. The amount of enzyme in the reaction and the activity of each enzyme was dependent on the presence of the corresponding activator. Furthermore, the addition of specific inhibitors abolished the phosphatase activity of the corresponding enzyme.

Example 6

Figure 8:
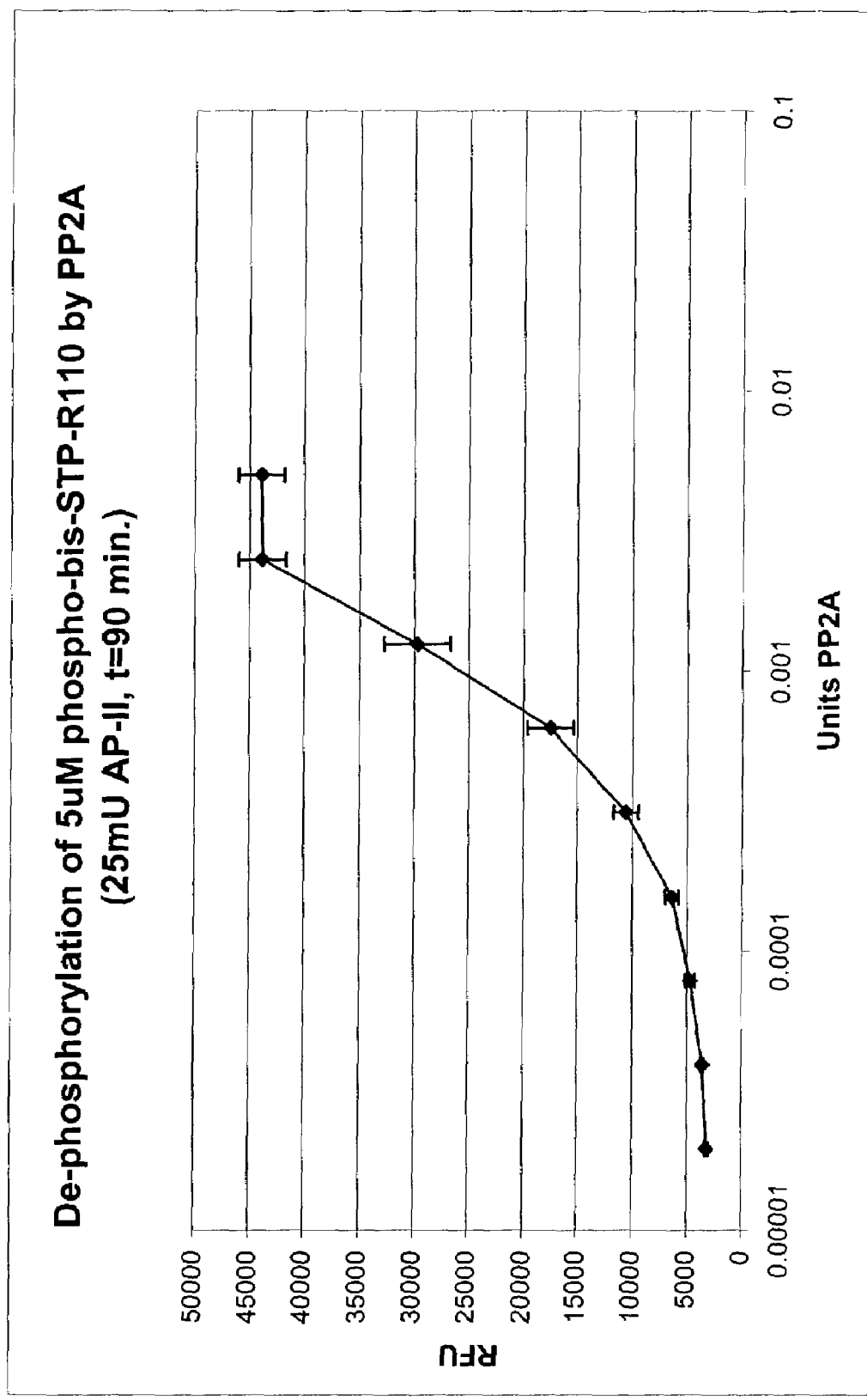
FIG. 8 is a graph showing detected output in RFU from a serine/threonine protein phosphatase assay using a different aminopeptidase (Aminopeptidase II) than the aminopeptidase used in FIGS. 1–7.

Detection of Phosphatase Activity using Rhodamine 110-Modified Peptide Substrate and Aminopeptidase II:

PP2A activity with STP-R110. Phosphatase activity of PP2A was tested using the same conditions as described in Example 5, above, except that PP2A was tested at concentrations ranging from 0.000001 mU to 0.01 mU, plus a control reaction containing no enzyme. Reactions were carried out at room temperature in 96-well plates for 10 minutes and were terminated with okadaic acid (9,10-Deepithio-9,10-didehydroacanthifolicin). In place of Aminopeptidase M, 25 mU of Aminopeptidase II was added and the reaction incubated for 90 minutes at room temperature. Fluorescence output was read as described earlier. FIG. 8 shows that an increase in phosphatase activity resulted in an increase in fluorescence. These data show that any aminopeptidase can be used to in the invention.

Example 7

Detection of Tyrosine Phosphatase Activity using R110-Modified Peptide Substrate and Aminopeptidase M:

CD45 and PTP-1B assays with PTK5-R110. Phosphatase reactions were carried out using either CD45, which is a recombinant human receptor protein tyrosine phosphatase, or PTP-1B, which is a soluble tyrosine phosphatase. Reactions were carried out in 50 ul volume containing 1 uM of phosphopeptide substrate bis-PTK5p-R110 (YIY($PO_3$)GAFKRRG (SEQ. ID. NO:6)-R110-GRRKFAG($PO_3$)YIY), 40 mM Tris-HCl, pH 7.5, 0.1 mg/ml BSA. Reactions were carried out in the presence of increasing concentrations of phosphatase (0–2 units of CD45, or 0–0.025 units of PTP-1B) for 10 minutes at room temperature in 96-well plates.

Figure 9:
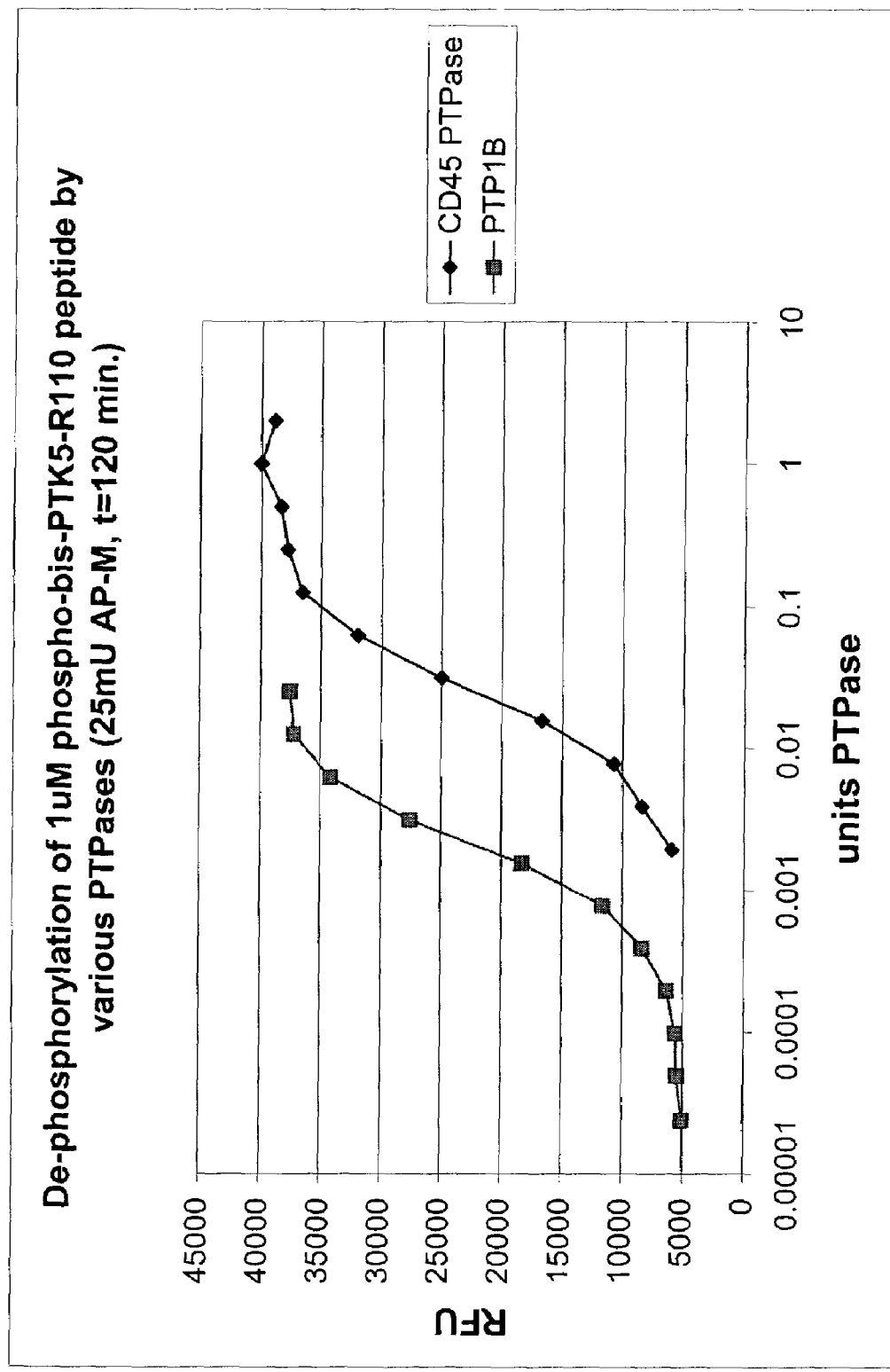
FIG. 9 is a graph showing detected output in RFU from a protein tyrosine phosphatase assay where the phosphatases added to the reaction were titrated.

Phosphatase reactions were terminated with 25 ul of a solution containing 40 mM Tris-HCl, pH 7.5, 0.1 mg/ml BSA, 300 uM $Na_3VO_4$, and 1 mU/ul of Aminopeptidase M. Reactions were incubated for additional 90 minutes at room temperature. Fluorescence was read as earlier described for Example 1. The results in FIG. 9 show that the increase in the fluorescence output is proportional to the amount of phosphatase added per reaction. The assay was also very sensitive to low concentrations of phosphatase. A similar profile was obtained with other tyrosine phosphatases, including YOP 51.

Example 8

Detection of Tyrosine Phosphatase Activity using R110-Modified Peptide Substrate and Aminopeptidase M:

PTP 1B activity with PTK5-R110. The effect of various inhibitors were tested on the dephosphorylation of bis-PTK5p-R110 by the enzyme tyrosine phosphatase PTP-1B. Sodium vanadate, ($Na_3VO_4$, a specific inhibitor of PTP-1B) and staurosporin (a known inhibitor of PKA but not of PTP-1B) were tested. Inhibitors were included in the reactions at concentrations ranging from zero inhibitor up to 50 uM. Phosphatase reactions were initiated by adding PTB-1B, which was added to each reaction at 25 mU/well. Control reactions containing no enzyme were also run. Phosphatase reactions were carried out generally as described in Example 7 for PTP-1B.

Figure 10:
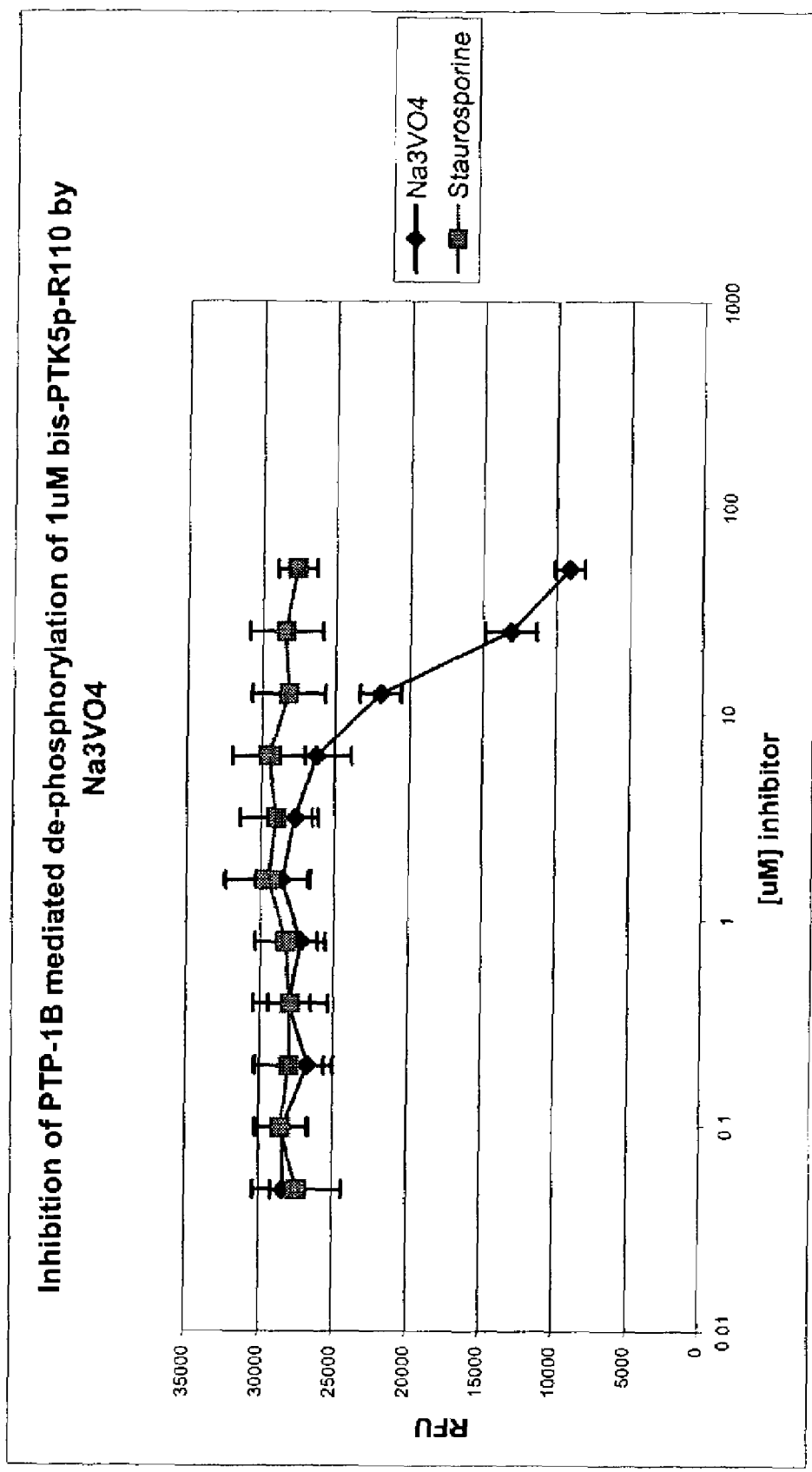
FIG. 10 is a graph showing detected output in RFU from a protein tyrosine phosphatase assay in the presence of certain inhibitors.

Phosphatase reactions were terminated with 25 ul of a solution of $Na_3VO_4$ and 25 mU/well of Aminopeptidase M. Reactions were incubated at room temperature for 60 minutes. Fluorescence was read as earlier described. The results in FIG. 10 show that dephosphorylation of the substrate by PTB-1B was only inhibited in the presence of increasing concentrations of $Na_3VO_4$ and not in the presence of staurosporin. Increasing concentrations of $Na_3VO_4$ resulted in a decreased fluorescence output indicating inhibition of PTP 1B enzyme activity, while staurosporin had no effect since fluorescence output was unchanged with increasing amounts of staurosporin.

Example 9

Detection of Ser/Thr Kinase using Luciferin Modified Peptide Substrate and Aminopeptidase M:

PKA Assay With LRRASLG-(Luciferin). Protein kinase assay is carried out at room temperature in a 50 ul volume in a 96-well plate, with the peptide substrate LRRASLG-Luciferin at 50 uM, and varying enzyme concentrations (0.001 to 1 unit) of protein kinase A in reaction buffer as described in Example 1. Reactions are terminated after 20 minutes by heat inactivation at 70° C. for 5 minutes. The reaction mixture is cooled off to room temperature, and 25 ul of detection buffer containing 50 mU/ul of Aminopeptidase M in 40 mM Tris HCl, pH 7.5 and 0.1 mg/ml BSA. The reaction is kept at room temperature for additional 60 minutes before optional termination by addition of actinonin at a final concentration of 2.5 uM. Luciferase (Promega Corporation) at 100 ug/ml in a 25 ul of steady glow buffer (Promega Corp.) is added, and then luminescence is read at 30 minutes in an Orion plate luminometer, Berthold Detection Systems (Pforzheim, Germany). Expression of enzyme activity is expected to be similar to that described for fluorescently labeled substrates shown in Example 1, i.e., a decrease in luminescence output in response to increase in enzyme concentration or activity.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A method for detecting kinase or phosphatase activity of a sample, the method comprising:
   (A) contacting the sample with a peptide substrate and at least one of a phosphate group donor and a phosphate group acceptor, wherein the substrate includes a reporter compound and amino acids;
   (B) adding an exopeptidase, wherein phosphorylation of the substrate affects cleavage by the exopeptidase; and
   (C) detecting output of the reporter compound, wherein the reporter compound exhibits a different output property when bound to at least one amino acid of the substrate when compared to when it is not bound to amino acids.

2. A method of claim 1, wherein the reporter compound comprises a fluorogenic compound.

3. A method of claim 2, wherein the fluorogenic compound is chosen from at least one of Rhodamine 110 and aminomethylcoumarin.

4. A method of claim 1, wherein the reporter compound comprises a luminogenic compound.

5. A method of claim 1, wherein adding the exopeptidase comprises adding an exopeptidase that hydrolyzes the substrate from an amino-terminal end of the substrate.

6. A method of claim 1, wherein the output of the reporter compound detected corresponds to a kinase activity.

7. A method of claim 6, wherein the substrate is a phosphate group acceptor.

8. A method of claim 1, wherein the substrate is a phosphate group donor.

9. A method of claim 1, wherein the output of the reporter compound detected corresponds to a phosphatase activity.

10. A method of claim 9, wherein the substrate is a phosphate group donor.

11. A method of claim 1, wherein the substrate is a phosphate group acceptor.

12. A method of claim 1, further comprising linking the substrate to a solid support.

13. A method of claim 12, wherein the substrate is linked to the solid support via a first functional group on the substrate and a second functional group on the solid support.

14. A method for detecting kinase or phosphatase activity of a sample, the method comprising:
   (A) contacting the sample with a peptide substrate and at least one of a phosphate donor and a phosphate acceptor, wherein the substrate includes a fluorogenic reporter compound and amino acids;
   (B) adding aminopeptidase M, wherein phosphorylation of the substrate affects cleavage by the aminopeptidase M; and
   (C) detecting output of the reporter compound, wherein the reporter compound exhibits a different output property when bound to at least one amino acid of the substrate when compared to when it is not bound to amino acids.

15. A method of claim 14, wherein the output of the reporter compound corresponds to a kinase activity.

16. A method of claim 14, wherein the output of the reporter compound corresponds to a phosphatase activity.

* * * * *